United States Patent
Huff et al.

(10) Patent No.: US 6,521,755 B1
(45) Date of Patent: Feb. 18, 2003

(54) PROCESS FOR PREPARING 10,11-METHANOBENZOSUBERANE DERIVATIVES

(75) Inventors: Bret Eugene Huff, Zionsville, IN (US); Michael Edward LeTourneau, Indianapolis, IN (US); Thomas Michael Wilson, Speedway, IN (US); Julie Kay Bush, Fishers, IN (US); Susan Marie Reutzel-Edens, Indianapolis, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 09/980,847

(22) PCT Filed: May 26, 2000

(86) PCT No.: PCT/US00/09826

§ 371 (c)(1),
(2), (4) Date: Nov. 15, 2001

(87) PCT Pub. No.: WO00/75121

PCT Pub. Date: Dec. 14, 2000

Related U.S. Application Data

(60) Provisional application No. 60/137,283, filed on Jun. 3, 1999.

(51) Int. Cl.$^7$ .................. C07D 295/088; C07D 401/12; C07D 241/12
(52) U.S. Cl. ...................... 544/336; 544/363; 544/381; 544/410; 568/808
(58) Field of Search ................ 544/363, 381, 544/336, 410

(56) References Cited

U.S. PATENT DOCUMENTS

| | | | |
|---|---|---|---|
| 4,235,871 A | | 11/1980 | Papahadjopoulos et al. |
| 4,501,728 A | | 2/1985 | Geho et al. |
| 4,749,703 A | * | 6/1988 | Uno et al. ............. 514/253 |
| 4,837,028 A | | 6/1989 | Allen |
| 5,011,472 A | | 4/1991 | Aebischer et al. |
| 5,023,252 A | | 6/1991 | Hseih |
| 5,643,909 A | | 7/1997 | Pfister et al. |
| 5,654,304 A | * | 8/1997 | Pfister et al. ............. 514/253 |

OTHER PUBLICATIONS

Dhainaut et al., J.Med.Chem. vol. 35, pp. 2481–2496 (1992).*
Suzuki et al., J.Med.Chem vol. 40, pp. 2047–2052 (1997).*
Kuzmich and Tew, "Detoxification Mechanisms and Tumor Cell Resistance to Anticancer Drugs," *Medical Research Reviews*, vol. 11, No. 2, pp. 185–217 (217).

Georges, Sharom, and Ling, "Multidrug Resistance and Chemosensitization: Therapeutic Implications for Cancer Chemotherapy," *Advances in Pharmacology*, vol. 1, pp. 185–200 (1990).

Berge, Bighley, and Monkhouse, "Pharmaceutical Salts," *J. Pharm. Sci.*, vol. 66, No. 1, pp. 1–19 (1997).

Section XIII, "Chemotherapy of Neoplastic Diseases" in Goodman and Gilman's *The Pharmacological Basis of Therapeutics*, Seventh Edition, pp. 1240–1306 (1985).

Childs, Brown, Anet, and Winstein, "A Dibenzohomotropylium Ion," *J. Am. Chem. Soc.*, vol. 94, No. 7, pp. 2175–2183 (1972).

Berti, *J. Org. Chem.*, vol. 22, p. 230 (1957).

Looker, *J. Org. Chem.*, vol. 33, No. 3, pp. 1304–1306 (1968).

Dykstra, Minielli, Lawson, *J. Med. Chem.* vol. 16, No. 9, pp. 1015–1020 (1973).

Bugle and Osteryoung *J. Org. Chem.*, vol. 44, No. 10, pp. 1719–1720 (1979).

Ashcroft and Joule, *Heterocycles*, vol. 16, No. 11, pp. 1883–1887 (1981).

Coyne and Cusic, *J. Med. Chem.*, vol. 17, No. 1, pp. 72–75 (1974).

Florence and Attwood, Physicochemical Principles of Pharmacy, $2^{nd}$ Ed., Chapman and Hall, New York, NY 1988, pp. 23–46.

March, *J. Ad. Org. Chem.*, $3^{rd}$ edition, 1985, John Wiley and sons, New York (cover page and table of contents only provided).

Larock, Comprehensive Organic Transformations, 1989, VCH publisher, New York cover page and table of contents, only provided.

Remington's Pharm. Sci., $17^{th}$ edition, 1985 table of contents, only provided.

* cited by examiner

*Primary Examiner*—Emily Bernhardt
(74) *Attorney, Agent, or Firm*—Elizabeth A. McGraw; Francis O. Ginah

(57) ABSTRACT

This invention provides a process to prepare 10,11-(optionally substituted)methanodibenzosuberane derivatives. The invention also provides an intermediate in this process.

15 Claims, 6 Drawing Sheets

13C CP/MAS NMR spectrum of Hydrate I (asterisks denote spinning sidebands)

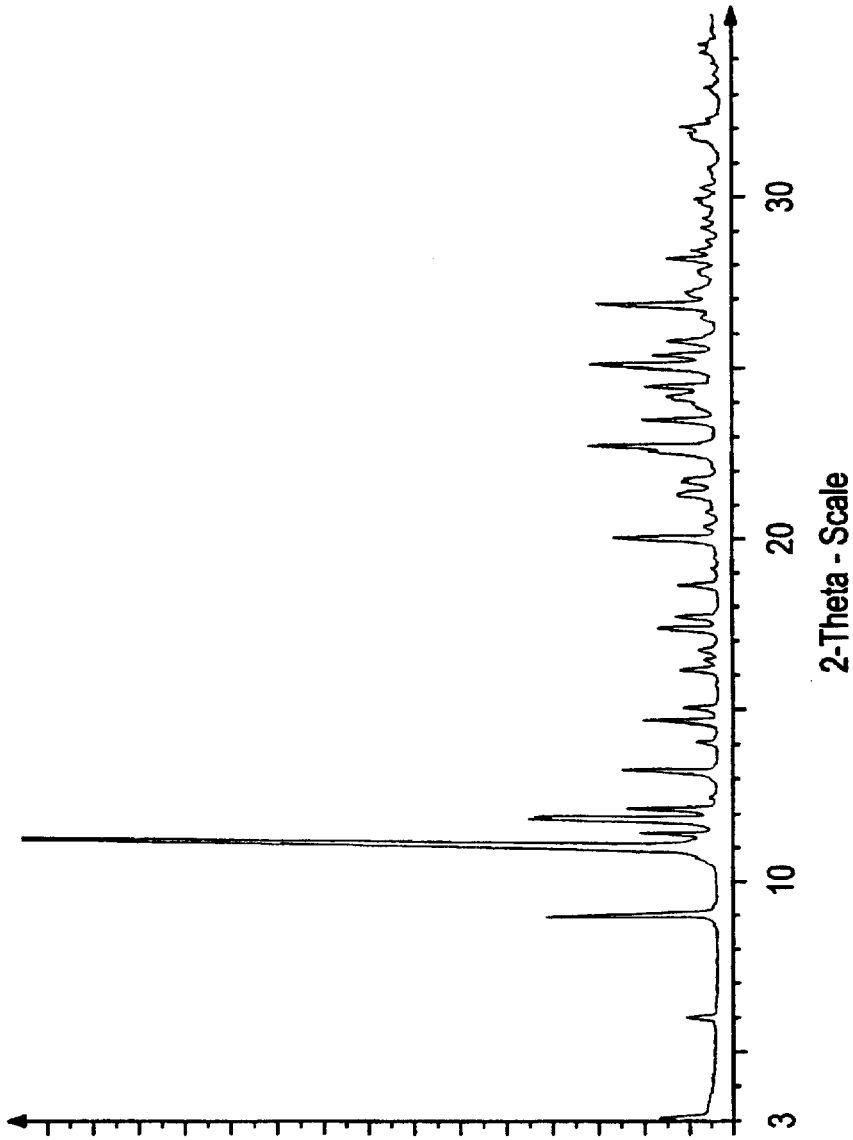

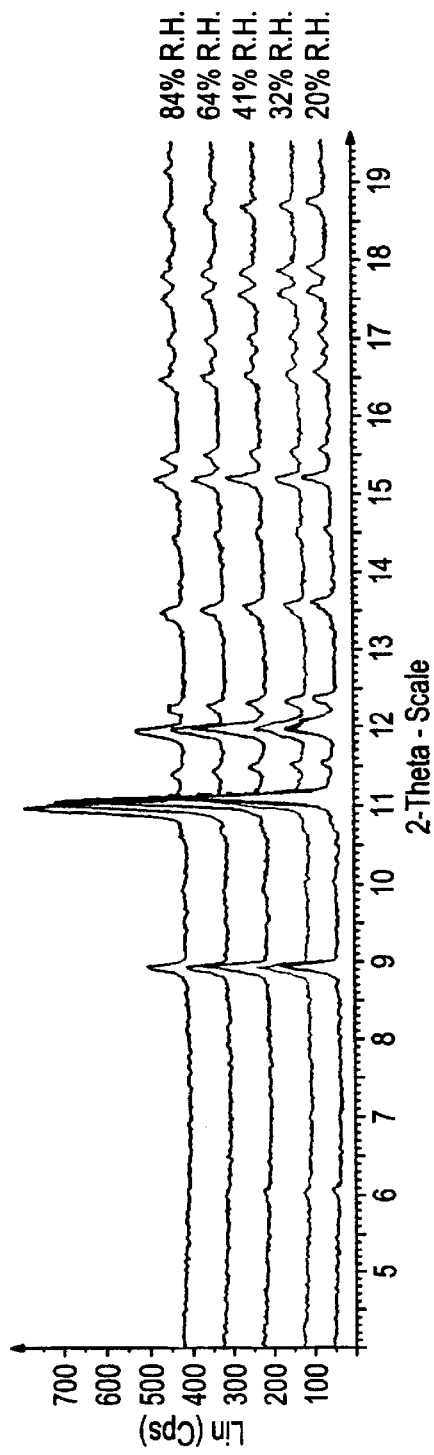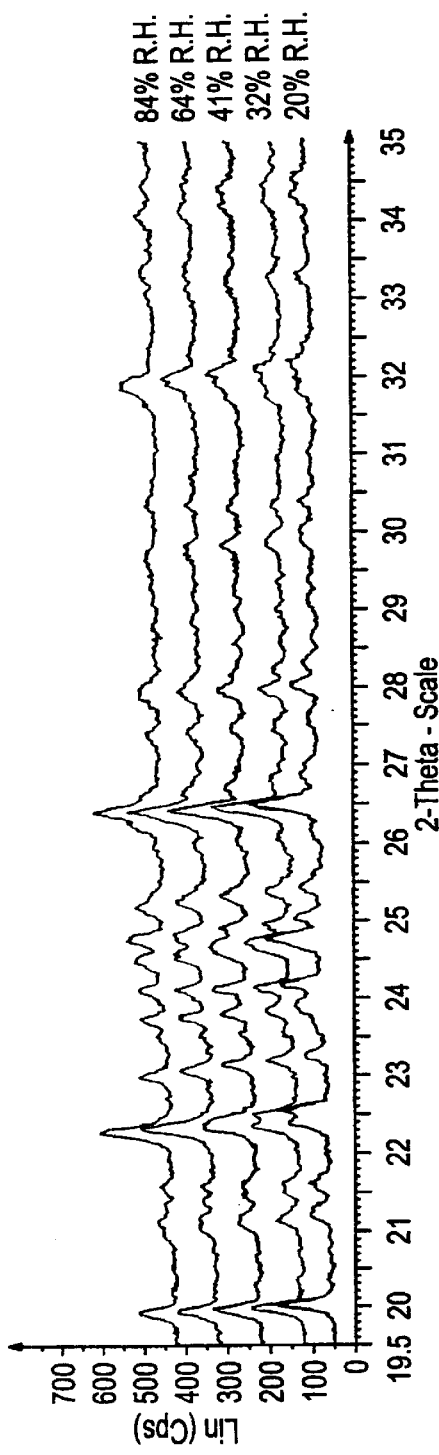

13C CP/MAS NMR spectra of representative solvates.

MeOH/H$_2$O

13C CP/MAS NMR spectra of representative solvates.

EtOH/H$_2$O $^{13}$C CP/MAS NMR spectra of representative solvates.

IPA/H$_2$O $^{13}$C CP/MAS NMR spectra of representative solvates.

n-PrOH H$_2$O

Experimental XRD patterns of the solvates: a) methanol solvate, b) ethanol solvate, c) IPA solvate, d) n-propanol solvate, e) THF solvate, f) acetone solvate, g) acetonitrile solvate, h) DMAC-acetone solvate, i) DMF solvate.

PROCESS FOR PREPARING 10,11-METHANOBENZOSUBERANE DERIVATIVES

This application claims the benefit of U.S. Provisional Application No. 60/137,283, filed Jun. 3, 1999.

Among the problems faced in certain types of drug therapy, including cancer chemotherapy and malaria drug therapy, is the phenomena of resistance to treatment regimens. The resistance means, for example, that cancerous tumors that responded well initially to a particular drug or drugs, later develop a tolerance to the drug(s). Drug resistance is the name given to the circumstance when a disease does not respond to a treatment drug or drugs. Drug resistance can be either intrinsic, which means the disease has never been responsive to the drug(s), or it can be acquired, which means the disease ceases responding to a drug or drugs that the disease had previously been responsive to. Multidrug resistance is a specific type of drug resistance that is characterized by cross-resistance of a disease to more than one functionally and/or structurally unrelated drugs. Multidrug resistance in the field of cancer, is discussed in greater detail in Kuzmich and Tew, "Detoxification Mechanisms and Tumor Cell Resistance to Anticancer Drugs," particularly section VII "The Multidrug-Resistant Phenotype (MDR)," *Medical Research Reviews,* Vol. 11, No. 2, 185–217, particularly 208–213 (1991); and in Georges, Sharom and Ling, "Multidrug Resistance and Chemosensitization: Therapeutic Implications for Cancer Chemotherapy," *Advances in Pharmacology,* Vol. 21, 185–220 (1990).

Treatment of drug and multidrug resistance typically involves the coadministration of a drug suitable for treatment of the disease and a compound which acts through various mechanisms to cause the drug suitable for treatment of a disease to begin and/or continue to function as a therapeutic agent.

U.S. Pat. No. 5,654,304 ('304), incorporated by reference herein, discloses a series of 10,11-(optionally substituted)methanodibenzosuberane derivatives useful in enhancing the efficacy of existing cancer chemotherapeutics and for treating multidrug resistance. (2R)-anti-5-{3-[4-(10,11-Difluoromethanodibenzosuber-5-yl)piperazin-1-yl]-2-hydroxypropoxy}quinoline trihydrochloride is disclosed in '304 and is currently under development as a pharmaceutical agent.

A crystalline form of this compound, which can be conveniently formulated for administration to patients, is highly desirable. Thus, there is a need to prepare (2R)-anti-5-{3-[4-(10,11-difluoromethanodibenzosuber-5-yl)piperazin-1-yl]-2-hydroxypropoxy}quinoline trihydrochloride as a pure, highly crystalline solid in order to fulfill exacting pharmaceutical requirements and specifications.

Preferably, such a crystalline compound will be readily formed and have favorable bulk or pharmaceutical characteristics. Examples of favorable bulk characteristic are drying times, filterability, solubility, intrinsic dissolution, thermal stability, and hygroscopicity. Examples of favorable pharmaceutical characteristics are purity and potency. Decreased organic solvents in the crystalline structure is favorable, due in part to potential solvent toxicity to the recipient as a function of the solvent. Furthermore, the process for preparing crystalline compounds also needs to be conveniently carried out on commercial scale.

Although the 10,11-methanedibenzosuberanes prepared by the procedures taught in '304 could be used as a pharmaceutical, "one cannot predict which compounds will be polymorphic" (Florence and Attwood, Physicochemical Principles of Pharmacy, 2$^{nd}$ Ed., Chapman and Hall, New York, N.Y., 1988, pages 23–24), it would be highly desired and advantageous to find a more crystalline form of (2R)-anti-5-{3-[4-(10,11-difluoromethanodibenzosuber-5-yl)piperazin-1-yl]-2-hydroxypropoxy}quinoline trihydrochloride having the advantageous properties described above. The preparation of the new crystalline form of the present invention fulfills these desirable features.

Additionally, there is need for an improved process for the preparation 10,11-(optionally substituted) methanodibenzosuberane derivatives which is more efficient and adaptable to large scale processing than those previously employed, for example in '304. Advantages of an improved process may include, for example, improved stereoselectivity, purity, and yield.

The present invention provides a process for preparing a compound of formula (1)

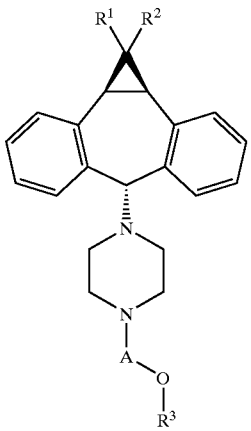

wherein

A is —CH$_2$—CH$_2$—, —CH$_2$—CHR$^a$—CH$_2$—, —CH$_2$—CHR$^a$—CH$_2$—CH$_2$—, and R$^a$ is OH;

R$^1$ is H, F, Cl, or Br;

R$^2$ is H, F, Cl, or Br; and

R$^3$ is heteroaryl or phenyl, each optionally substituted with F, Cl, Br, CF$_3$, CN, NO$_2$, or OCHF$_2$;

or the pharmaceutically acceptable salts thereof, comprising the steps of:

(a) reacting a compound of formula (4)

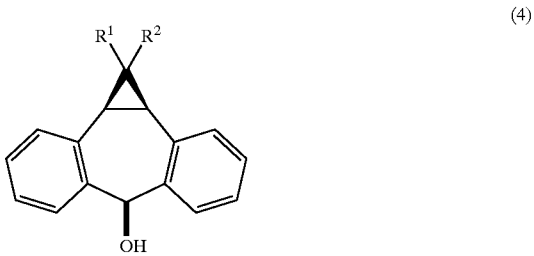

with a nucleophile source to form a compound of formula (5)

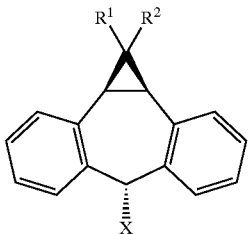

(5)

wherein X is a leaving group;
(b) reacting a compound of formula (5) with pyrazine to provide a compound of formula (6)

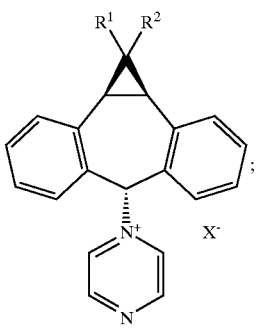

(6)

(c) reducing the compound of formula (6) to provide a compound of formula (8):

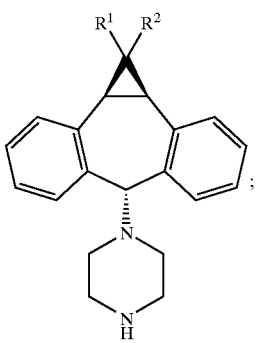

(8)

(d) reacting a compound of formula (8) with either:
(i) an epoxy compound of formula (9)

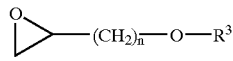

(9)

wherein $R^3$ is as defined above, and n is an integer 1 or 2; or
(ii) a halo compound of formula (10)

(10)

wherein $R^3$ is as defined above, $X^1$ is halo, and m is 2, 3 or 4; and
(e) optionally forming a pharmaceutically acceptable salt from the compound produced in step (d).

The present invention also provides an improved process for preparing a compound of formula (4):

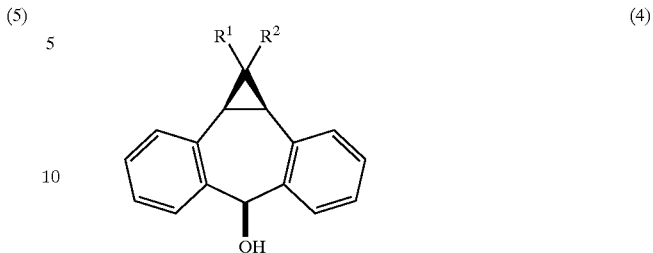

(4)

comprising reacting dibenzosuberenone with an alkali trihaloacetate to produce an intermediate 10,11-(optionally substituted)methanodibenzosuberone and reducing said intermediate, wherein both reactions are performed in one operational step.

The ability to perform both reactions in one operational step is an advantage over the prior art. U.S. Pat. No. 5,654,304 teaches a step-wise preparation of the 10,11-(optionally substituted)methanodibenzosuberol, beginning with preparation and isolation of 10,11-(optionally substituted)methanodibenzosuberone from dibenzosuberenone (2) in diglyme and sodium trihaloacetate (e.g., sodium chlorodifluoroacetate) in diglyme at a temperature of 160° C. to 165° C. followed by reduction of the intermediate 10,11-(optionally substituted)methanodibenzosuberone (3) to afford the corresponding 10,11-(optionally substituted) methano dibenzosuberol.

Additionally, the present invention contemplates a compound of formula (6)

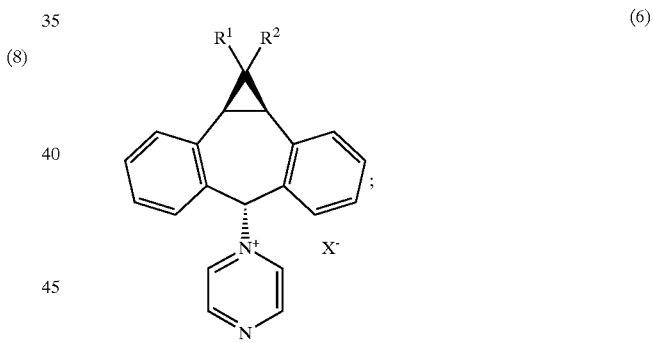

(6)

wherein $R^1$ and $R^2$ are independently H, F, Cl or Br and X is leaving group selected from the group consisting of Br, Cl, OMs, and OTs.

Moreover, the present invention provides a novel hydrate crystal form of (2R)-anti-5-{3-[4-(10,11-difluoromethanodibenzosuber-5-yl)piperazin-1-yl]-2-hydroxypropoxy}quinoline trihydrochloride ("Hydrate I"), having an X-ray diffraction pattern which comprises the following peaks corresponding to d spacings: 7.95+/−0.04 Å when obtained at 22±2° C. and 31±10% relative humidity from a copper radiation source.

The present invention also provides the novel hydrate a characterized above, having an X-ray diffraction pattern further comprising the following peaks: 9.93, 4.45, and 3.36+/−0.04 Å when obtained at 22±2° C. and 31±10% relative humidity from a copper radiation source.

The present invention further provides a method of treatment for a drug resistant disease comprising coadministering to a mammal in need thereof a resistance modulating amount of Hydrate I and an effective amount of a treatment drug for said drug resistant disease.

The present invention further provides a method of treatment for a multidrug resistant disease comprising coadministering to a mammal in need thereof a multidrug resistance modulating amount of Hydrate I and an effective amount of a treatment drug for said multidrug resistant disease.

The present invention further provides a method for enhancing bioavailability of a drug to the brain, comprising coadministering to a mammal in need thereof a therapeutically effective amount of said drug and Hydrate I sufficient enough to allow said drug to cross the blood-brain barrier and enter the brain.

The present invention further provides a method for enhancing oral bioavailability of a drug comprising administering to a mammal in need thereof a therapeutically effective amount of said drug and Hydrate I sufficient enough to allow said drug to be transported across the gastrointestinal tract and enter the bloodstream.

The present invention further provides a solvate of (2R)-anti-5-{3-[4-(10,11-difluoromethanodibenzosuber-5-yl)piperazin-1-yl]-2-hydroxypropoxy}quinoline trihydrochloride.

BRIEF DESCRIPTION OF THE FIGURES

FIG. 2 depicts a representative XRD pattern of Hydrate I.

FIG. 3 depicts the XRD pattern, showing systematic shifts in peak positions as a function of the variable water content in the lattice of Hydrate I.

DETAILED DESCRIPTION OF THE INVENTION

Definitions and General Parameters

Figure 1:
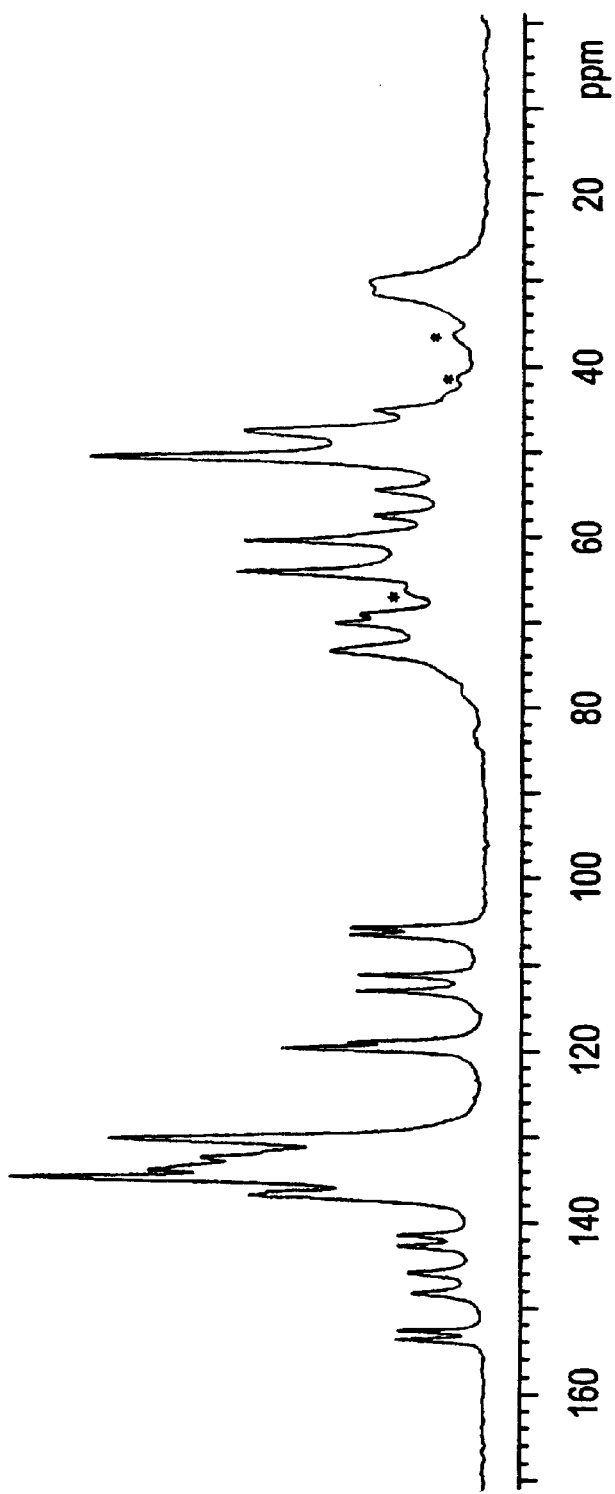
FIG. 1 is a representative solid state NMR spectrum of Hydrate I.
Figure 4A:
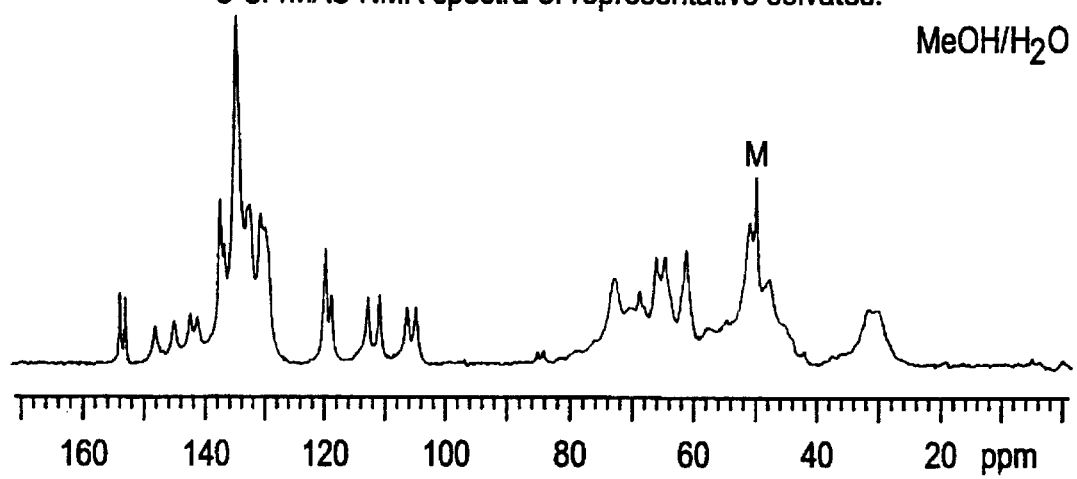
FIGS. 4 are representative solid state NMR spectra for representative solvates.
Figure 4B:
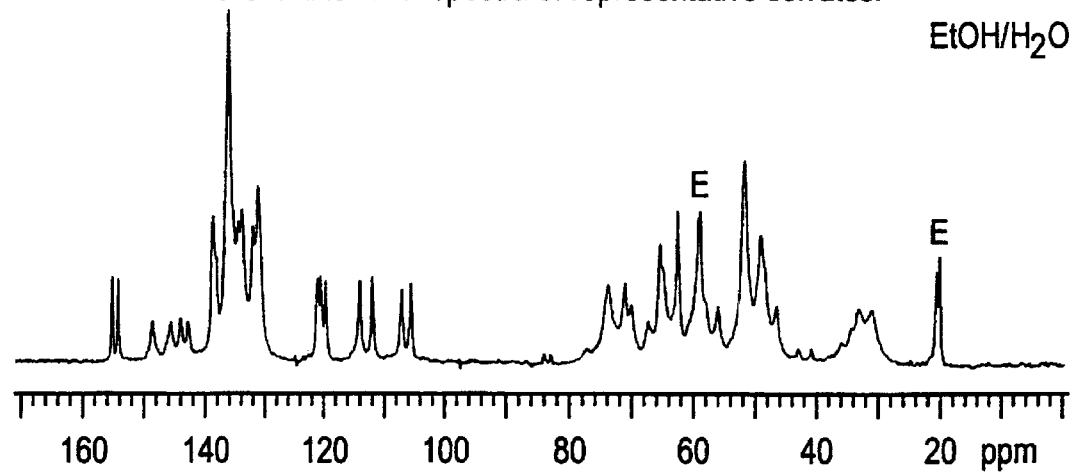
Figure 4C:
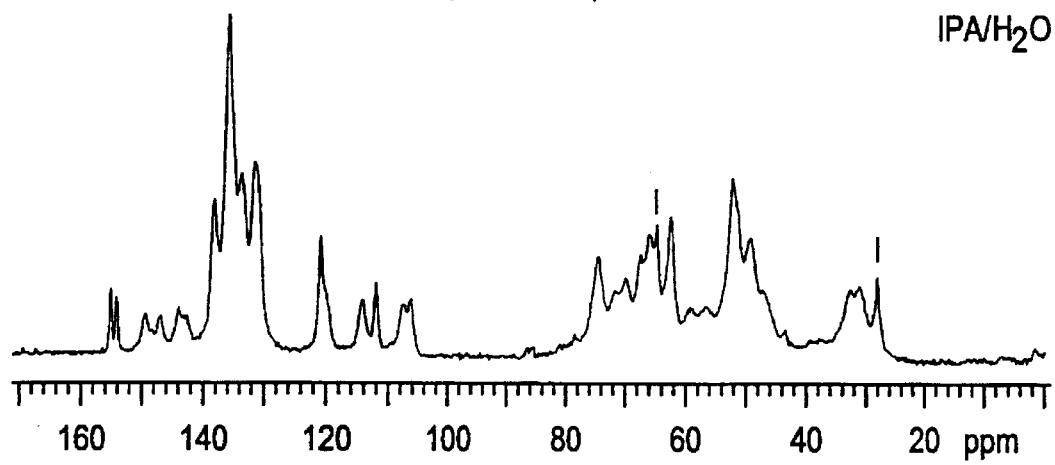
Figure 4D:
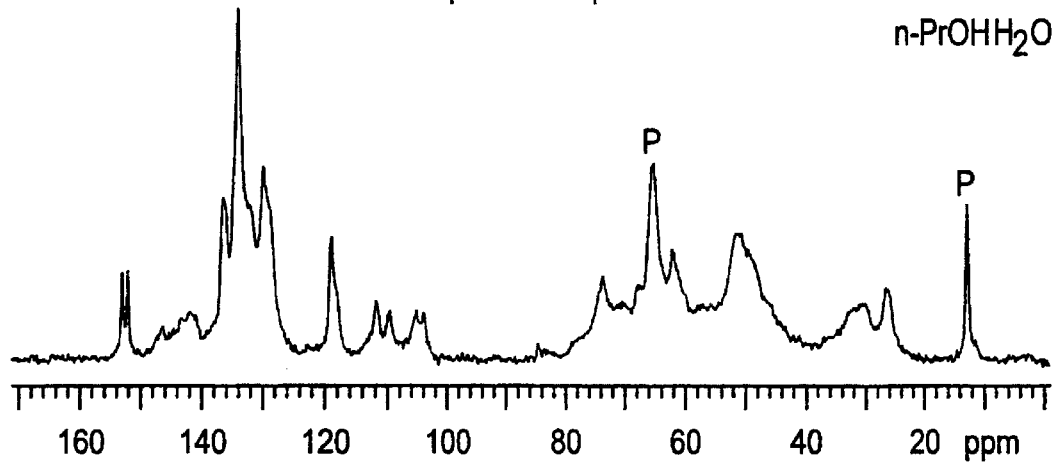
Figure 5:
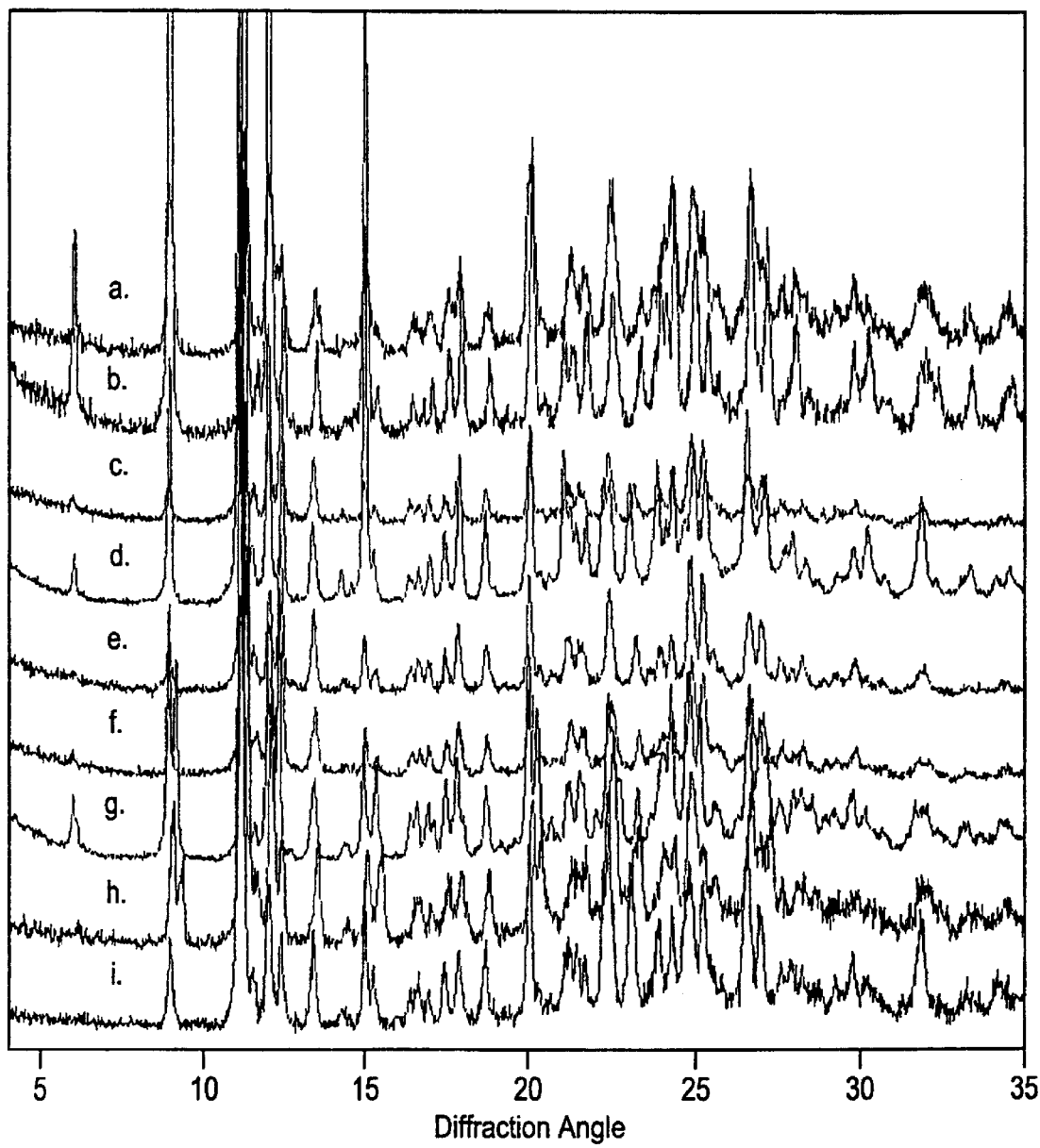
FIG. 5 depicts representative XRD patterns for representative solvates.

The following definitions are set forth to illustrate and define the meaning and scope of the various terms used to describe the invention herein.

In general, the term "pharmaceutical" when used as an adjective means substantially non-toxic to living organisms. For example, the term "pharmaceutical salt" as used herein, refers to salts of the compounds of formula I which are substantially non-toxic to living organisms. See, e.g., Berge, S. M, Bighley, L. D., and Monkhouse, D. C., "Pharmaceutical Salts", *J. Pharm. Sci.*, 66:1, 1977. Typical pharmaceutical salts include those salts prepared by reaction of the compounds of formula I with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

The term "cancer therapeutic agent" refers to compounds, which have an anticancer therapeutic effect. Such compounds are non-antimetabolites such as anthracycline group antibiotics, e.g. adriamycin, daunomycin, doxorubicin, or acrasinomycin A; actinomycin group antibiotics, e.g. actimomycin C or D; chromomycin group antibiotics, e.g. mithramycin or toyomycin; vincoalkaloids, e.g. vincristine, or vinblastine; meitansins; podophyllotoxin derivatives, e.g. VP16-213; homoharintonin; angwindin; bruceantin; neocarcinostatin; anthromycin; mitomycin C; and cisplatin. Additional cancer therapeutic agents may be found in the medical literature, for example, Section XIII, "Chemotherapy of Neoplastic Diseases" in Goodman and Gilman's *The Pharmacological Basis of Therapeutics,* Seventh Edition, pages 1240–1306 (1985).

The term "bioavailability" refers to the degree and rate at which a drug, or other substance, becomes available to a target tissue within a mamal.

The term "coadministering" means a disease treatment drug and Hydrate I are given to a mammal. The drug and Hydrate I are given to a mammal simultaneously or at different times.

The term "drug resistance" refers to the circumstance when a disease does not respond to a treatment drug or drugs. Drug resistance can be either intrinsic, which means the disease has never been responsive to the drug or drugs, or it can be acquired, which means the disease ceases responding to a drug or drugs that the disease had previously responded to.

"Multidrug resistance" means a specific type of drug resistance characterized by cross-resistance of a disease to more than one functionally and/or structurally unrelated drugs. Multidrug resistance can be either intrinsic or acquired.

The term "acid addition salt" refers to a salt of a compound of formula I prepared by reaction of a compound of formula I with a mineral or organic acid. For exemplification of pharmaceutical acid addition salts see, e.g., Berge, S. M, Bighley, L. D., and Monkhouse, D. C., *J. Pharm. Sci.,* 66:1, 1977. Since compounds of this invention can be basic in nature, they accordingly react with any of a number of inorganic and organic acids to form pharmaceutical acid addition salts.

Acids commonly employed to form acid addition salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid, mono-, di- and tricarboxylic acids and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycolate, tartrate, methanesulfonate, propanesulfonate, naphthalene-1-sulfonate, naphthalene-2-sulfonate, mandelate and the like.

In the general formulae of the present document, the general chemical terms have their usual meanings. For example, the term "halo" refers to halogen, for example, fluoro, bromo, chloro and iodo.

The term "alkyl" refers to a fully saturated monovalent radical containing only carbon and hydrogen, and which may be a cyclic, branched or straight chain radical. This term is further exemplified by radicals such as methyl, ethyl, t-butyl, pentyl, pivalyl, heptyl and adamantyl.

The term "lower alkyl" refers to branched or straight chain monovalent alkyl radical of one to six carbon atoms, and optionally to a cyclic monovalent alkyl radical of three to six carbon atoms. This term is further exemplified by such radicals as methyl, ethyl, n-propyl, isopropyl, n-butyl, t-butyl, i-butyl (or 2-methylpropyl), cyclopropyl-methyl, i-amyl, n-amyl, and hexyl.

The term "alkylene" refers to a fully saturated divalent radical containing only carbon and hydrogen, and which may be a branched or straight chain radical. This term is further exemplified by radicals such as methylene, ethylene, n-propylene, t-butylene, i-pentylene, and n-heptylene.

The term "lower alkylene" refers to a divalent alkyl radical of one to six carbon atoms. This term is further exemplified by such radicals as methylene, ethylene, n-propylene, i-propylene, n-butylene, t-butylene, i-butylene (or 2-methylpropylene), isoamylene, pentylene, and n-hexylene.

The term "aryl" refers to a phenyl or naphthyl group which may be optionally substituted with 1–3 substituents independently selected from the group consisting of fluoro, chloro, bromo, trifluoromethyl, cyano, nitro and difluoromethoxy.

The term "heteroaryl" refers to a monovalent aromatic carbocyclic radical having at least one hetero atom, such as N, O, or S, within the ring, such as quinolinyl, benzofuranyl, pyridyl, pyrazinyl, carbazolyl, norharmanyl, harmanyl, indazolyl, 5-nitroindazolyl, benzimidazolyl, benzotriazolyl, anthranilyl, lutidinyl, collidinyl, acridinyl and isoquinolinyl. The heteroaryl group may optionally be substituted with 1–3 substituents independently selected from the group consisting of fluoro, chloro, bromo, trifluoromethyl, cyano, nitro and difluoromethoxy.

"Optional" or "optionally" means that the subsequently described event or circumstance may or may not occur, and that the description includes instances where said event or circumstance occurs and instances in which it does not.

The term "leaving group" as used herein refers to a group cleavable from the substrate molecule during a reaction step and comprises a halo group, sulfonates (e.g., mesylate (OMs) or tosylate (OTs)) and the like known in the art as leaving groups.

The term "nucleophile source" as used herein describes a group capable of effecting a nucleophilic substitution on an alcohol. Such groups include halogenic acids such as HCl, HBr or HI and sulfonic acids, sulfonic anhydrides or sulfonic acid halides e.g., methanesulfonic acid chloride.

The term "hydrate" as used herein describes the crystalline lattice which can contain variable amounts of water depending upon the relative humidity in the storage conditions. Preferably, Hydrate I contains from about 9% to about 13% water and less than about 1% organic solvents.

As used herein the terms "5H-dibenzo[a,d]cyclohepten-5-one," and "dibenzosuberenone" are synonymous.

The terms and abbreviations used herein have their normal meanings unless otherwise designated, for example, "°C." refers to degrees Celsius; "N" refers to normal or normality; "mmol" refers to millimole or millimoles; "g" refers to gram or grams; "d" refers to density, "min." refers to minutes, "mL" means milliliter or milliliters; "M" refers to molar or molarity; "HPLC" refers to high performance liquid chromatography; "mm" refers to millimeters; "cm" refers to centimeters; "nm" refers to nanometers; and "$t_r$" refers to retention time.

The present invention provides a process for preparing a compound of formula (1)

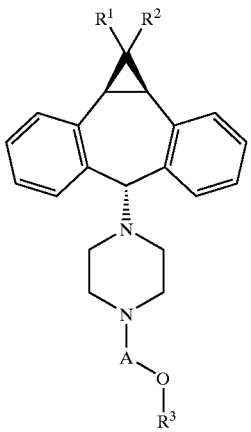

wherein

A is —CH$_2$—CH$_2$—, —CH$_2$—CHR$^a$—CH$_2$—, —CH$_2$—CHR$^a$—CH$_2$—CH$_2$—, and R$^a$ is OH;

R$^1$ is H, F, Cl, or Br;

R$^2$ is H, F, Cl, or Br; and

R$^3$ is heteroaryl or phenyl, each optionally substituted with F, Cl, Br, CF$_3$, CN, NO$_2$, or OCHF$_2$;

or the pharmaceutically acceptable salts thereof, comprising the steps of:

(a) reacting a compound of formula (4)

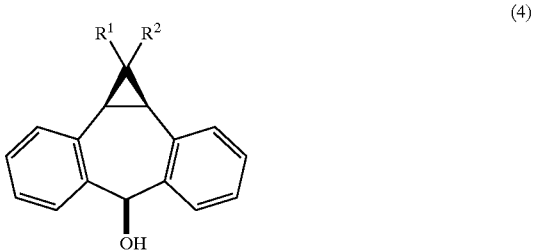

with a nucleophile source to form a compound of formula (5)

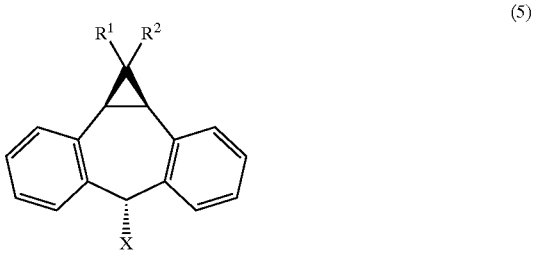

wherein X is a leaving group;

(b) reacting a compound of formula (5) with pyrazine to provide a compound of formula (6)

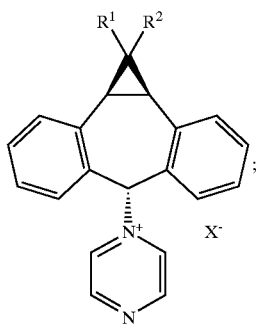

(6)

(c) reducing the compound of formula (6) to provide a compound of formula (8):

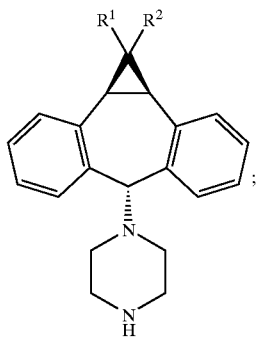

(8)

(d) reacting a compound of formula (8) with either:
(i) an epoxy compound of formula (9)

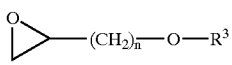

(9)

wherein $R^3$ is as defined above, and n is an integer 1 or 2; or (ii) a halo compound of formula (10)

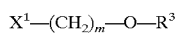

(10)

wherein $R^3$ is as defined above, $X^1$ is halo, and m is 2, 3 or 4; and (e) optionally forming a pharmaceutically acceptable salt from the compound produced in step (d).

In a preferred aspect the present invention is a procedure as shown in scheme 1, to afford 10,11-(optionally substituted) methanodibenzosuberol in a single operational step from dibenzosuberenone.

Scheme 1

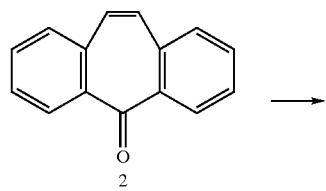

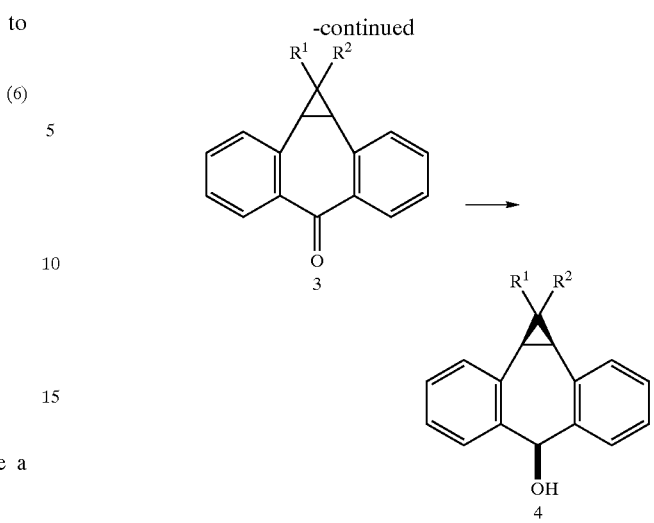

This embodiment of the present invention provides the advantage of efficiency, ease of processing, reduced cost of manufacture and a more environment-friendly process over the teaching of U.S. Pat. No. 5,654,304. These advantages are made possible by the use of, and increased solubility of lithium trihaloacetate salt. The higher reaction concentration incident to increased solubility of the lithium salt and reduction in solvent volumes compared to prior art provide increased throughput and reaction rate. These advantages are also made possible by the higher reaction temperature made possible by the use of triglyme, which also enhances the rate of reaction. For specific reaction conditions see steps (a) and (b) of scheme 4.

Preferably 1-(aryloxy or heteroaryloxy)-2,3-epoxypropane, 1-(aryloxy or heteroaryloxy)-3,4-epoxybutane, or aryloxy- or heteroaryloxyalkyl halide, and a 1-[10,11-(optionally substituted)methano-dibenzosuber-5-yl] piperazine are combined to give the corresponding 10,11-methanodibenzosurberane derivative of Formula (1).

A further embodiment of this invention provides a process for preparing the anti isomer of the novel 10,11-(optionally substituted)methanodibenzosuberyl pyrazinium salt compound of formula (6). This embodiment of the invention is illustrated in scheme 2 below:

Scheme 2

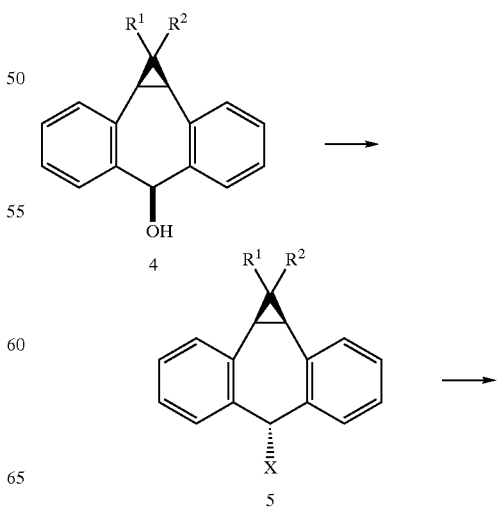

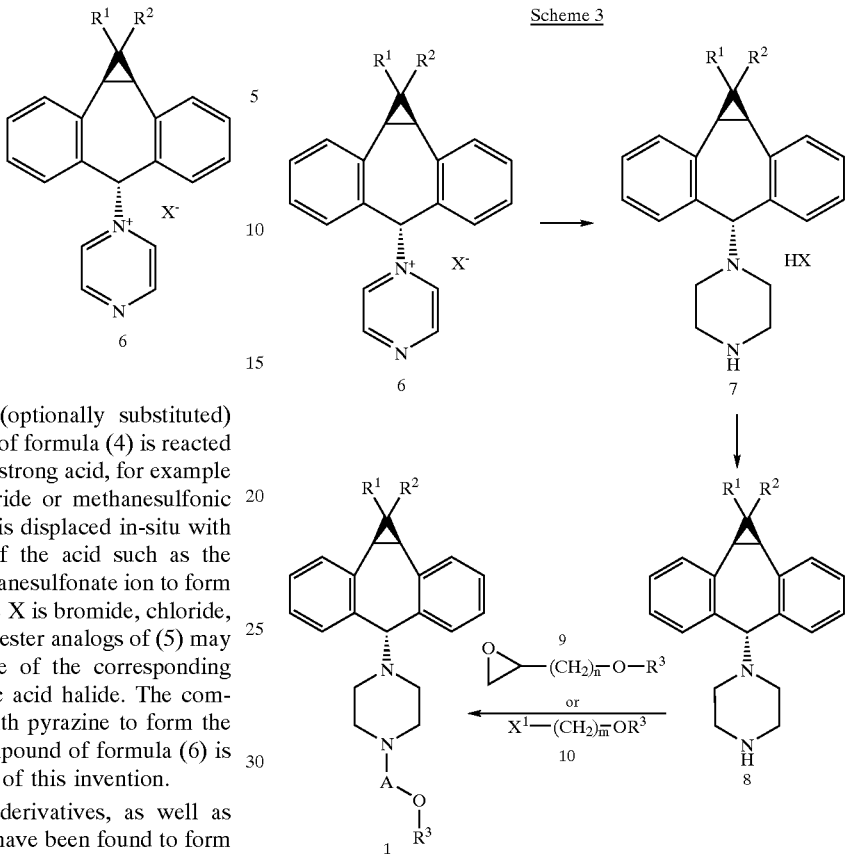

Scheme 3

In this embodiment the 10,11-(optionally substituted) methanodibenzosuberol compound of formula (4) is reacted with a nucleophile source such as a strong acid, for example hydrogen bromide, hydrogen chloride or methanesulfonic acid. The incipient hydronium ion is displaced in-situ with the nucleophilic conjugate base of the acid such as the bromide ion or chloride ion or methanesulfonate ion to form the compound of formula (5) where X is bromide, chloride, or methanesulfonate. The sulfonate ester analogs of (5) may be preferably accessed by the use of the corresponding sulfonic acid anhydride or sulfonic acid halide. The compound of formula (5) is reacted with pyrazine to form the compound of formula (6). The compound of formula (6) is novel and is a further embodiment of this invention.

Dibenzo[5.1.0]bicyclooctadiene derivatives, as well as derivatives of related ring systems have been found to form stable carbocations. It has been reported that treatment of 2,3,5,6-dibenzo-4-hydroxy[5.1.0]bicycloocta-2,5-diene with fluorosulfuric acid at −78° C. or sulfuric acid at room temperature provided solutions of the corresponding dibenzohomotropylium ion, which was characterized by NMR (see Childs, R. F.; Brown, M. A.; Anet, F. A. L.; Winstein, S. *J. Am. Chem. Soc.* 1972, 94, 2175. See also: Berti, G. *J. Org. Chem.* 1957, 22, 230. Looker, J. J. *J. Org. Chem.* 1968, 33, 1304.) Typically, nucleophilic reactions at the benzylic position in these systems will proceed primarily by a $S_N1$-type mechanism, giving rise to mixtures of syn and anti products via a carbocation intermediate. The present invention, however, provides the anti bromide analog of (5) which is obtained as the exclusive product in good yield from syn alcohol precursor (4). The corresponding anti alcohol also gave rise to the anti bromide analog of (5) exclusively under the same bromination conditions. General teachings on halogenation or sulfonation of alcohols are given in reference texts such as March, J., *Advanced Organic Chemistry*, 3rd edition, 1985, John Wiley and Sons, New York, N.Y., and Larock R. C., *Comprehensive Organic Transformations*, 1989 VCH Publishers, New York, N.Y.

The 10,11-(optionally substituted) dibenzosuberylhalide or sulfonate (5) obtained as described above is then reacted with pyrazine in a suitable solvent, such as dichloromethane, to form the pyrazinium salt compound of formula (6). Nucleophilic reactions of nitrogen-containing aromatic heterocycles, particularly pyrazine, with bromide analog of (5), result in exclusive formation of anti quaternary salts, for example the pyrazinium salt compound of formula (6).

A further embodiment of this invention is represented by scheme 3 below;

This embodiment of the invention, utilizes the 10,11-(optionally substituted)methanodibenzosuberyl pyrazinium salt compound of formula (6) obtained from the processes of the invention as described above. In this embodiment the 10,11-(optionally substituted)methanodibenzosuberyl pyrazinium salt compound of formula (6), is reduced using conditions capable of reducing the pyrazine ring to afford the piperazine compound of formula (8). Reduction of the pyrazinium salt compound of formula (6) can be accomplished by hydrogenation or metal hydride reductions, for example lithium tetrahydroaluminum hydrides, sodium borohydride and other similar reducing agents known to one skilled in the art. Preferred reducing agents for the purpose of this invention include lithium borohydride and sodium borohydride. The reduction using lithium or sodium borohydride is typically aided by the addition of trifluoroacetic acid. The reduction product is typically isolated as the acid salt by treatment of the product solution with concentrated aqueous or anhydrous acid, for example concentrated hydrochloric acid. Reductions of pyrazinium salts and pyridinium salts have been reported in the literature. See for example, Dykstra, S. J.; Minielli, J. L.; Lawson, J. E. *J. Med. Chem.* 1973, 16, 1015. Bugle, R. C.; Osteryoung, R. A. *J. Org. Chem.* 1979, 44, 1719. Ashcroft, W. R.; Joule, J. A. *Heterocycles* 1981, 16, 1883.

The 10,11-(optionally substituted)methano dibenzosuberylpiperazine acid salt (7) is neutralized to afford the free base compound of formula (8) employing an inorganic base such as sodium hydroxide, sodium carbonate, bicarbonate, potassium carbonate and the like. Most preferred is the use of powdered potassium carbonate in protic solvents such as ethanol. One skilled in the art is aware that aqueous inorganic bases may also be employed. Furthermore, one skilled in the art can appreciate that mild organic bases, such as triethylamine, may also be employed to effect this neutralization.

The compound of formula (8) is reacted with either the compound of formula (9) or the compound of formula (10) to afford the compound of formula (1). Preparation of compounds of formula (8) and (9) are described in U.S. Pat. Nos. 5,643,909 and 5,654,304, incorporated herein by reference. The use of the compounds of formula (8) wherein $R^3$ is the quinolinyl group is preferred. Most preferred is the use of compounds of formula (8) wherein the group $R^3$ is the quinolin-5-yl group. Improved procedures for preparing the preferred embodiment of compound (8) wherein $R^3$ is the quinolin-5-yl group are disclosed infra in this application. The compound of formula (1) may be optionally reacted with a pharmaceutically acceptable acid to form the acid salt. Preferred acids include hydrogen chloride, hydrogen bromide, sulfuric acid, camphorsulphonic acid and the like.

A general preparative route to the compounds of formula (1), according to the present invention, is given in Scheme 4 below:

Various embodiments of this invention are incorporated in Scheme 4. For example, in scheme 4, steps (a) and (b) encompass one embodiment, steps (a) through (d) encompass a further embodiment and steps (a) through (g) encompass a further embodiment of this invention wherein all embodiments have been described supra. The starting material for the purpose of this invention is 5H-dibenzo[a,d] cyclohepten-5-one (dibenzosuberenone), which is commercially available, e.g., from Aldrich Chemical Company, Milwaukee, Wis. Other reactants are likewise commercially available or may be readily prepared by one of skill in the art.

Step (a): A solution of an alkali trihaloacetate is added over a period of about 4 to about 8 hours, preferably about 6 hours, to a solution of dibenzosuberenone with stirring and under nitrogen while maintaining the reaction temperature preferable from about 160 to about 165° C. The reaction mixture is brought to room temperature, then poured into

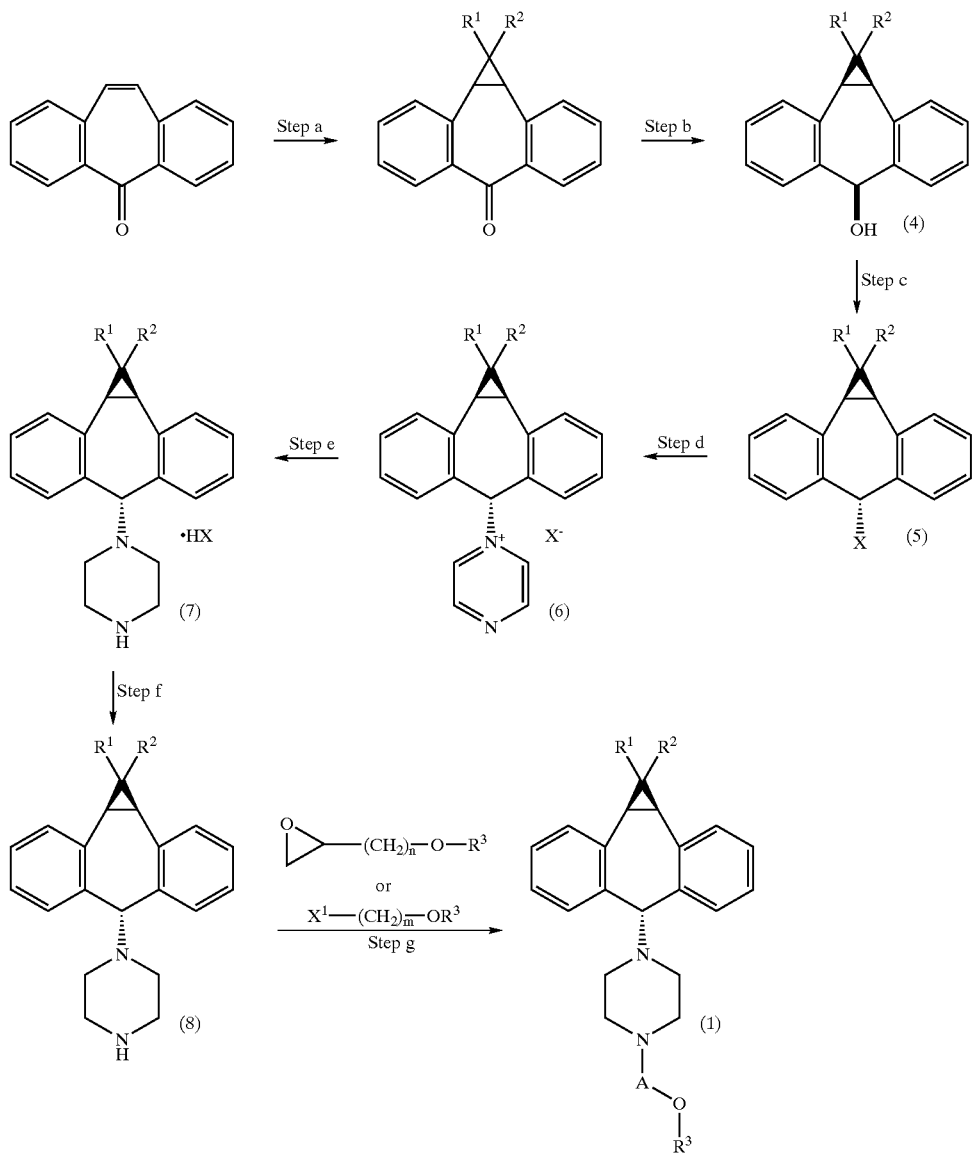

Scheme 4 water and extracted, preferably with ether. The desired 10,11-(optionally substituted)methanodibenzosuberone is isolated and purified by conventional means. For example, the organic phase is washed with water, dried, preferably over $Na_2SO_4$, evaporated, and the residue is recrystallized.

Examples of alkali trihaloacetates for use in step (a) are sodium chlorodifluoroacetate, methyl trichloroacetate, ethyl trifluoroacetate. The preferred alkali trihaloacetate is dependent upon the desired substituents for $R^1$ and $R^2$.

Preferred solvents are diglyme, benzene, and petroleum ether.

The skilled artisan would appreciate that other reaction temperatures may be employed depending upon the reactants used. For example, see Coyne and Cusic, "Aminoalkyldibenzo[a,e]cyclopropa[c]cycloheptene Derivatives. A Series of Potent Antidepressants," J. Med. Chem., 1974, Vol. 17, No. 1, 72–75.

Alternatively, 10,11-methanodibenzosuberone compounds where $R^1$ and $R^2$ are not identical, such as when $R^1$ H and $R^2$ Cl, can be prepared as described by Coyne et al., supra. The compound of formula (2) where $R^1$ and $R^2$ are both hydrogen can be prepared as described in Coyne and Cusic, et al., supra.

Step (b): A solution of the 10,11-(optionally substituted) methanodibenzosuberone, from step (a), in a solvent, preferably tetrahydrofuran in methanol, is cooled and a reducing agent, preferably lithium borohydride or sodium borohydride, sufficient to effect reduction is added in portions. The reaction mixture is allowed to come to room temperature and stirred for about 1 to about 5 hours, preferably about 2 hours, then poured into water. The product is isolated and purified by conventional means to give the corresponding 10,11-(optionally substituted) methanodibenzosuberol of formula 3.

The skilled artisan would appreciate that other hydride reducing agents, including chiral and achiral reducing agents and controlled hydrogenations should effect this reduction.

Combined Steps (a) and (b) Procedure: To a solution of 5H-dibenzo[a,d]cyclohepten-5-one (dibenzosuberenone) in triethylene glycol dimethyl ether heated from about 180° C. to about 210° C. is slowly added chlorodifluoroacetic acid, lithium salt in ethylene glycol dimethyl ether. The ethylene glycol dimethyl ether is distilled from the reaction as the salt addition proceeds. After the dibenzosuberenone has been consumed as determined by analytical methods known to one skilled in the art, the reaction is cooled to about ambient temperature and then combined with a mixture of ethyl acetate and diatomaceous earth. The solids are removed by filtration and washed with ethyl acetate. The washes and filtrate are combined and the ethyl acetate removed by concentration under vacuum. The concentrate is cooled to about 15 to about 30° C., followed by addition of sodium borohydride or lithium borohydride solution. After stirring for about 2 h the reaction is quenched by careful addition of a solution of conc. HCl in methanol-water (approximately 5–20%). The suspension is stirred for about 30 min and the crude product is collected by filtration. The filter cake is washed with 1:1 methanol-water and dried to a dark brown solid. The crude product is then slurried in methylene chloride, filtered and dried to afford syn-10,11-(optionally substituted) methanodibenzosuberol.

Step (c): A solution of the 10,11-(optionally substituted) methanodibenzosuberol, from step (b), in a solvent, preferably heptane, is cooled followed by addition of a source of a leaving group, such as a hydrogen halide, methanesulfonic acid chloride, or the like. Bromination, for example, is effected by the addition of hydrogen bromide while maintaining a temperature from about 30° C. to about 100° C., for about 2 to about 5 hours, preferably about 4 hours. The reaction mixture is then evaporated to dryness, affording the corresponding 5-bromo-10,11-(optionally substituted) methanodibenzosuberane.

The use of hydrogen bromide is preferred over other halogenating agents such as hydrogen chloride or thionyl chloride to afford the anti-stereoisomer preferentially. The 5-halo-10,11-difluoromethanodibenzosuberane may, without further purification, be reacted with pyrazine. Alternatively the anti-isomer of the corresponding 5-halo-10,11-(optionally substituted)methanodibenzosuberane may be purified and isolated before being subjected to treatment with pyrazine. The use of trifluoromethanesulfonic acid chloride or p-toluene sulfonic acid chloride or corresponding anhydride affords the corresponding compound of formula (5) where X is trifluoromethyl or p-toluene-sulfonate ester.

Step (d): The reaction of the anti 5-halo-10,11-(optionally substituted)methanodibenzosuberane compound of formula (5) or its sulfonate analog, with pyrazine is with or without solvent. Preferred solvents include dimethyl sulfoxide, dimethyl sulfoxide/methylene chloride, methylene chloride, ethyl acetate, and tetrahydrofuran. The reaction mixture is evaporated to dryness and the desired anti-1-[10,11-(optionally substituted)methanodibenzosuber-5-yl]-pyrazinium salt compound of formula (6) may be isolated and purified.

Combined Steps (c) and (d): The steps of forming the 5-halo-10,11-(optionally substituted) methanodibenzosuberane or its sulfonate analogs of formula (5) and subsequently forming the 1-[10,11-(optionally substituted) methanodibenzosuber-5-yl]pyrazinium salt (formula 6), can be combined into one operational step by distillative solvent exchange following formation of the 5-halo-10,11-(optionally substituted)methanodibenzosuberane or its sulfonate analogs, and followed by addition of pyrazine.

Step (e): Preferably the anti-1-[10,11-(optionally substituted) methanodibenzosuber-5-yl]pyrazinium salt of formula (6) is reduced to the desired piperazine compound of formula (8) with, for example, a hydride reducing agent. Preferably the reducing agent is sodium borohydride or lithium borohydride. However, the skilled artisan will appreciate that other reducing agents are capable of effecting the desired reduction.

The reaction mixture may be treated with, for example, hydrogen chloride or hydrogen bromide to form the corresponding salt compound of formula (7) for ease of isolation as the crystalline salt. It should be noted that one skilled in the art may perform a controlled hydrogenation or utilize other reducing agents such as chiral reducing agents, biocatalytic reductions or other methods known in the art to effect reduction of the pyrazinium salt to the piperazine compound of formula (8).

Step (f): A solution of the anti-1-[10,11-(optionally substituted)methanodibenzosuber-5-yl]piperazine acid salt of compound (7) and potassium hydroxide in a solvent (e.g., aqueous ethanol, or aqueous propanol, or isopropanol) is refluxed for about 0.5 to about 2 hours, preferably about 1 hour, then cooled. The cooled reaction mixture is concentrated, diluted with water, extracted, dried (preferably over $K_2CO_3$), and the organic phase is evaporated to give the corresponding anti-1-[10,11-(optionally substituted) methanodibenzosuber-5-yl]piperazine compound of formula (8).

Combined Steps (f) and (g): The desired compound of formula (1) can be prepared by performing the processes of steps (f) and (g) of scheme (4) sequentially or in one operational step according to the methods of this invention. Alternatively the compound (7) product of this invention can be utilized to prepare compounds of formula (1) according to the examples and methods known in the art, (e.g. the methods described in U.S. Pat. No. 5,654,304).

For example, a suspension of anti-1-[10,11-(optionally substituted)methanodibenzosuber-5-yl]piperazine acid salt of compound of formula (7) and powdered sodium carbonate in N,N-dimethylformamide or aqueous sodium hydroxide or the like is stirred at ambient temperature for 1 to 3 hours, preferably 1 hour. (2R)-1-(5-quinolinyloxy)-2,3-epoxypropane compound of formula (9) is added and the reaction mixture is heated to about 40° C. to about 100° C., preferably from about 65° C. for about 10 to about 30 hours, preferably about 19 hours. Temperature and time may vary depending on reagents utilized. HPLC analysis is utilized to indicate total consumption of the piperazinyl compound of formula (8). The mixture is allowed to cool to about room temperature, filtered through a plug of silica gel, and eluted with ethanol. The filtrate is concentrated and heated to about 65° C. with stirring. A solution of HCl in ethanol is added drop-wise over about 10 minutes and the resultant product solution is seeded, causing the trihydrochloride salt to precipitate. The mixture is cooled to ambient temperature and stirred for about 2 hours. The precipitate is filtered, washed with ethanol, and dried in vacuo at about 50° C. to give the crude trihydrochloride salt which can be further purified by recrystallization from methanol/ethyl acetate to provide in the case where $R^1$ and $R^2$ are each fluorine, the compound (2R)-anti-1-[4-(10,11-difluoromethano-10,11-dihydro-5H-dibenzo[a,d]cyclohepten-5-yl)-piperazin-1-yl]-3-quinolin-5-yloxy)-propan-2-ol trihydrochloride. It should be understood that one of skill in the art may react the compound of formula (8) directly with the compound of formula (9) or formula (10) to obtain the compound of formula (1).

A preferred embodiment of this invention is one where the $R^3$ group is the "quinolin-5-yl" group, and is represented by the structure:

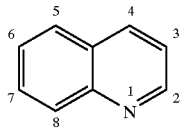

with a point of attachment at the 5-position counting from the nitrogen atom and used synonymously with the term "5-quinolyl."

Preferred are the processes according to the invention for preparing compounds of Formula (1) where $R^1$ and $R^2$ are fluoro. Also preferred are the processes according to the invention for preparing compounds of formula (1) where A is 2-hydroxypropylene and $R^3$ is quinolin-5-yl. Further preferred are those processes, which combine the above-mentioned features.

Another preferred aspect of the invention provides a procedure that combines steps (c) and (d) of scheme 4 to afford 1-[10,11-(optionally substituted) methanodibenzosuber-5-yl]-pyrazinium salt (formula (6)) in a single operational step from the 1-[10,11-(optionally substituted)methanodibenzosuberol (4).

Preferred is the process according to the invention for preparing the compound (2R)-5-{3-[4-(10,11-difluoromethanodibenzosuber-5-yl)piperazin-1-yl]-2-hydroxypropoxy}quinoline.

A most preferred embodiment of this invention comprises the preparation of (2R)-anti-5-{3-[4-(10,11-difluoromethanodibenzosuber-5-yl)piperazin-1-yl]-2-hydroxypropoxy}quinoline acid salt (1b),

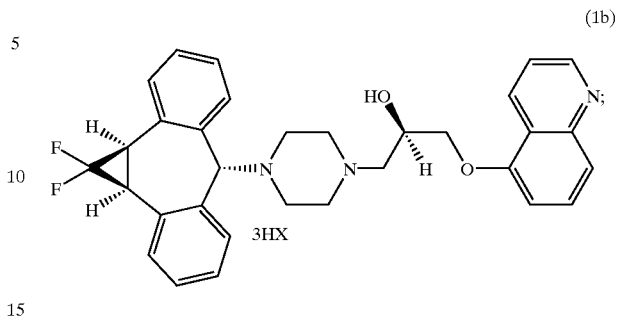

where HX is an acid selected from the group comprising of hydrogen chloride, hydrogen bromide, methane sulfonic acid, camphorsulfonic acid, p-toluene sulfonic acid, and sulfuric acid.

Optional Preparation of Salts of Formula (1)

The compounds of formula (1) can be converted to the corresponding acid addition salts. The conversion is accomplished by treatment with a stoichiometric amount of an appropriate acid, such as hydrochloric acid (e.g., 3 molar equivalents to form the trihydrochloride salt). Typically, the free base is dissolved in a polar organic solvent, such as methanol or ethanol, and the acid is added in water, methanol or ethanol. The temperature is maintained at 0° C. to 50° C. The corresponding salt precipitates spontaneously or can be brought out of solution with a less polar solvent.

The acid addition salts of the compounds of formula (1) can be decomposed to the corresponding free base by treatment with an excess of a suitable base. Suitable bases include for example, ammonia and sodium bicarbonate, typically in the presence of an aqueous solvent, and at a temperature between 0° C. and 50° C. The free base is isolated by conventional means, such as extraction with an organic solvent.

EXAMPLES

The following preparations and example(s) are illustrative only and are not intended to limit the scope of the invention in any way.

Preparation 1

(R)-1-(5-Quinolinyloxy)-2,3-epoxypropane

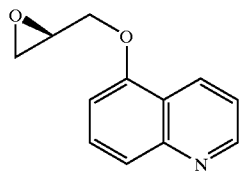

A mixture of 5-hydroxyquinoline (5.60 g, 38.6 mmol), (R)-glycidyl nosylate (10.0 g, 38.6 mmol), powdered potassium carbonate (11.7 g, 84.9 mmol), and N,N-dimethylformamide (100 mL) was stirred at ambient temperature until HPLC analysis (40% acetonitrile/60% of a 0.5% aqueous ammonium acetate solution, 1 mL/min, 1=230 nm, Zorbax RX-C8 25 cm×4.6 mm column) indicated complete disappearance of glycidyl nosylate (approximately 6 hours). The reaction mixture was filtered through paper and the filter cake was washed with 200 mL of a 3:1 mixture of MTBE and methylene chloride. The filtrate was washed with 200 mL of water and the aqueous layer was extracted four times with 100 mL of 3:1 MTBE/methylene chloride. The combined organic layers were dried over 30 grams of magnesium sulfate and the dried solution was then stirred with 50 grams of basic alumina for 30 minutes. The alumina was removed by filtration and the filter cake was washed with 200 mL of 3:1 MTBE/methylene chloride. The filtrate was concentrated to a volume of 100 mL. 300 mL of MTBE was added, and the solution was again concentrated to 80 mL. After heating to 50° C., the solution was treated with 160 mL of heptane drop-wise over 15 minutes, allowed to cool to 40° C., and seeded, causing the formation of a crystalline precipitate. The mixture was stirred for two hours at ambient temperature and then at 0–5° C. for an additional 2 hours. The crystals were filtered, washed with cold heptane, and dried to provide 5.68 g (73.2%) of (2R)-1-(5-quinolinyloxy)-2,3-epoxypropane as white needles.

mp 79–81° C.

$[\alpha]^{25}_D$ -36.4° (c 2.1, EtOH)

$^1$H NMR (500 MHz, CDCl$_3$) δ2.83 (dd, J=4.8, 2.7 Hz, 1H), 2.97 (m, 1H), 3.48 (m, 1H), 4.10 (dd, J=11.0, 6.0 Hz, 1H), 4.43 (dd, J=11.0, 2.7 Hz, 1H), 6.85 (d, J=7.8 Hz, 1H), 7.38 (dd, J=8.5 Hz, 4.1 Hz, 1H), 7.59 (m, 1H), 7.71 (d, J=8.5 Hz, 1H), 8.61 (m, 1H), 8.90 (m, 1H).

Preparation 2

1-(4-Benzofurazanyloxy)-2,3-epoxypropane

Sodium hydride (620 mg; 60% oil dispersion) was added in portions to benzofurazan-4-ol (1.74 g) in dimethylformamide (30 ml). The mixture was heated at 50° C. for 30 min. Epibromohydrin (1.6 ml) was added and the mixture was heated at 60° C. for 2 hours. The reaction mixture was poured into water and extracted with ethyl acetate. The organic phase was washed with water, dried over Na$_2$SO$_4$, and evaporated. The residue was chromatographed on silica gel (50% ethyl acetate/hexane) to give 1-(4-benzofurazanyloxy)-2,3-epoxypropane (1.6 g), mp 75° C.

Example 1

(2R)-anti-1-[4-(10,11-difluoromethano-10,11-dihydro-5H-dibenzo[a,d]cyclohepten-5-yl)-piperazin-1-yl]-3-quinolin-5-yloxy)-propan-2-ol trihydrochloride

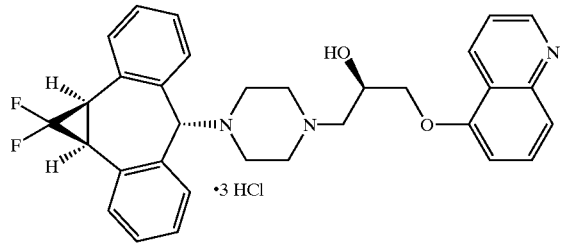

·3 HCl

Preparation of the above compound is exemplified in the following preparative steps.

Step a 10,11-Difluoromethanodibenzosuberone

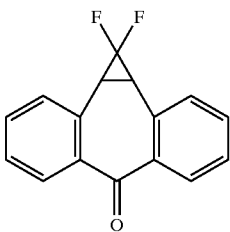

A solution of sodium chlorodifluoroacetate (350 g) in diglyme (1400 mL) was added dropwise over 4 to 8 hours, preferably over 6 hours, to a solution of dibenzosuberenone (25 g) in diglyme (500 mL), with overhead stirring and under nitrogen, maintaining the reaction temperature at 160–165° C. Heating was continued until the dibenzosuberenone was satisfactorily consumed (90–100%) as determined by analytical techniques such as Gas Chromatography or Thin Layer Chromatography known to one skilled in the art. The reaction mixture was then cooled to room temperature, poured into water (1.8 L) and extracted with ether (1.8 L). The organic phase was washed with water, dried over Na$_2$SO$_4$, and evaporated. The residue was recrystallized from ethanol, then from acetone/hexane to give 14 g of 10,11-difluoromethanodibenzosuberone, mp 149.6° C. Flash chromatography of the combined mother liquors on silica gel, eluting with 20% acetone/hexane, gave an additional 6.5 g of the desired material.

Gas Chromatography (GC) Conditions: Column JW Scientific DB-1, Initial Temperature 150° C. for 5 min, 10° C./min ramp, Final temp 250° C. for 5 min. $t_R$: desired product, 11.5 min; starting material, 12.3 min.

Step b 10,11-Difluromethanodibenzosuberol

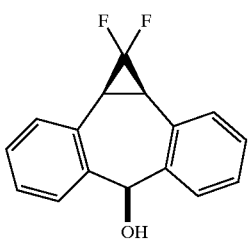

A solution of 10,11-difluoromethanodibenzo-suberone (20.4 g) in THF/MeOH (1:2, 900 ml) was cooled in an ice bath. Sodium borohydride (12 g) was added in portions. The cooling bath was removed, the reaction mixture was stirred at ambient temperature for 2 hours, and poured into water.

The product was filtered off, washed with water, and dried to give 20 g of syn 10,11-difluromethanodibenzosuberol.

mp 230.1–230.6° C.

Optional Combined Steps (a) and (b)

(10,11-Difluoromethanodibenzosuberol)

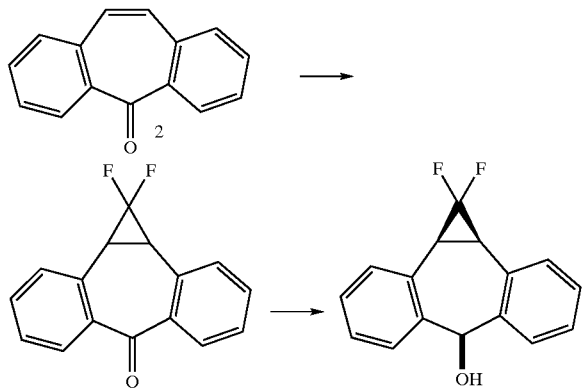

To a solution of 103.1 g (0.500 mol) of dibenzosuberenone (2) in 515 mL of triethylene glycol dimethyl ether heated to 180° C. was added, over 7 hours, 293.3 g (2.15 mol) of chlorodifluoroacetic acid lithium salt (as a 53% by weight solution in ethylene glycol dimethylether). The ethylene glycol dimethylether was allowed to distill from the reaction as the salt addition proceeded. The GC analysis of an aliquot indicated that all of the dibenzosuberenone had been consumed. The reaction was cooled to ambient temperature and then combined with 400 mL of ethyl acetate and 75 g of diatomaceous earth. The solids were removed by filtration and washed with 300 mL of ethyl acetate. The washes and filtrate were combined and the ethyl acetate was removed by concentration under vacuum leaving 635 g of dark liquid. The dark liquid was cooled to 18° C. and to this was added, over 15 min, 6.62 g (0.175 mol) of sodium borohydride (as a 12% by wt solution in 14 M NaOH). After stirring for 2 h the reaction was quenched by careful addition of 900 mL of a 1:3.5:4.5 solution of conc. HCl-methanol-water. The suspension was stirred for 30 min and the crude product was collected by filtration, washed with 600 mL of 1:1 methanol-water and dried to 126.4 g of dark brown solid. The crude product was slurried with 600 mL of methylene chloride, washed twice with 150 mL portions of methylene chloride, and dried to 91.6 g (71%) of 10,11-difluoromethanodibenzosuberol as a solid.

Gas Chromatography (GC) Conditions: Column JW Scientific DB-1, Initial Temperature 150° C. for 5 min, 10° C./min ramp, Final temp 250° C. for 5 min. $t_R$: intermediate, 11.5 min; desired product (alcohol), 11.9 min; starting material, 12.3 min.

Step c 5-bromo-10,11-difluoromethanodibenzosuberane

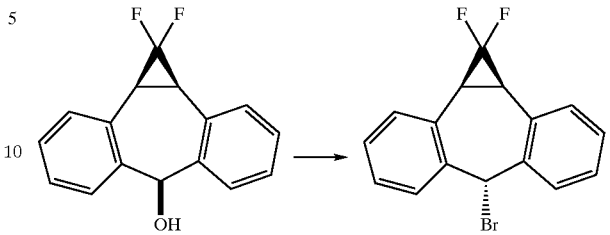

A slurry of the 10,11-difluoromethanodibenzo-suberol (3.0 g, 11.6 mmol, 1.0 equiv.) in heptane (24 mL) was treated with 48% HBr (1.58 mL, 14.0 mmol, 1.2 equiv.) and the reaction was heated at reflux with vigorous stirring for 2.5 hr. Solvent was then removed by atmospheric distillation (bp 95–98° C.) until c.a. 9 mL of distillate was collected. The reaction was cooled and treated with EtOAc (15 mL), $Na_2SO_4$ (1.5 g) and activated charcoal (750 mg). The mixture was stirred at RT for 15 min and filtered through hyflo. The filter cake was washed with 50:50 EtOAc:heptane (3×3 mL) and the filtrate was concentrated in vacuo to provide the product as a crystalline solid.

mp 119° C. (3.46 g corr., 93%)

$^1$HNMR (500 MHz $CDCl_3$) δ7.20–7.41 (8H, m), 5.81 (1H, s), 3.41 (2H, d, J=12.5 Hz)

$^{13}$CNMR (126 MHz $CDCl_3$) δ141.3, 141.2, 133.5, 130.1, 129.8, 128.3, 128.2, 112.9, 110.6, 110.5, 108.3, 53.6, 30.2, 30.1, 30.0

Anal. Calcd. For $C_{16}H_{11}BrF_2$: C, 59.84; H, 3.45. Found: C, 60.13; H, 3.50.

Combined Steps (c) and (d)

anti-1-[10,11-difluoromethanodibenzosuber-5-yl]-pyrazinium hydrobromide salt

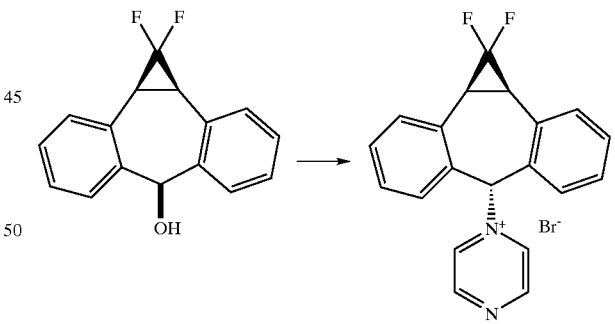

A stirred slurry of the 10,11-difluorodibenzo-methanosuberol (56.2 g of 91.8 wt %, or 51.6 g corr., 0.2 mol) in heptane (420 mL) was treated with 48% HBr (27.2 mL, 0.24 mol, 1.2 equiv.) and the thick slurry was heated at reflux with vigorous stirring. After 1.5 hr at reflux, the solvent was removed by atmospheric distillation to provide approximately 50% concentration. The reaction was cooled and diluted with EtOAc. Activated charcoal and $Na_2SO_4$ were added. After stirring at RT for 1 hour, the mixture was filtered through a pad of hyflo and the filter-cake was rinsed with 50:50 EtOAc:heptane. The filtrate was concentrated by vacuum distillation. The residue was diluted with EtOAc (200 mL) and concentrated in vacuo until ~200 mL of distillate was collected. The residue was diluted to 100 mL with EtOAc and treated with pyrazine (48.0 g, 0.6 mol, 3.0 equiv) and DMSO (50 mL), resulting in an endotherm to 6° C. The solution was warmed to 30–32° C. and stirred for 18 hours. The reaction mixture was diluted with methyl t-butyl ether (MTBE) (500 mL) and stirred for 15 min. Light-yellow solid was filtered, washed with MTBE (200 mL) and dried to provide the pyrazinium salt analog, anti-1-[10,11-difluoromethanodibenzosuber-5-yl]-pyrazinium hydrobromide.

m.p. 165° C. (68.2 g, 85%)

$^1$HNMR (500 MHz DMSO-$d_6$) δ9.46 (2H, d, J=2.7 Hz), 8.77 (2H, t, J=1.7 Hz), 7.74 (2H, d, J=7.5 Hz), 7.42–7.55 (6H, m), 7.27 (1H, s), 3.19 (2H, d, J=12.6 Hz)

$^{13}$CNMR (126 MHz DMSO-$d_6$) δ152.5, 135.8, 135.4, 134.4, 133.2, 132.1, 129.9, 129.6, 112.9, 110.6, 108.3, 77.4, 28.7, 28.6; FD MS: m/e 321 (M–Br)

Anal. Calcd. For $C_{20}H_{15}BrF_2N_2$: C, 59.87; H, 3.77; N, 6.98.

Found: C, 59.84; H, 3.66; N, 6.83.

Alternatively the anti isomer of the 5-halo-10,11-(optionally substituted) methanodibenzosuberane halogenation product could be prepared and isolated by the procedure of preparation 3, before being subjected to treatment with pyrazine.

Step e 1,1-difluoro-6-[1-piperazinyl]-1,1aa,6a,10ba-tetrahydrodibenzo[a,e]cyclopropa[c]cycloheptene hydrochloride (or) ((6S,1aS,10bR)-1,1-difluoro-1,6,10b,1a-tetrahydrodibenzo[b,e]cyclopropa[1,2-f][7]annulen-6-yl)piperazine hydrochloride

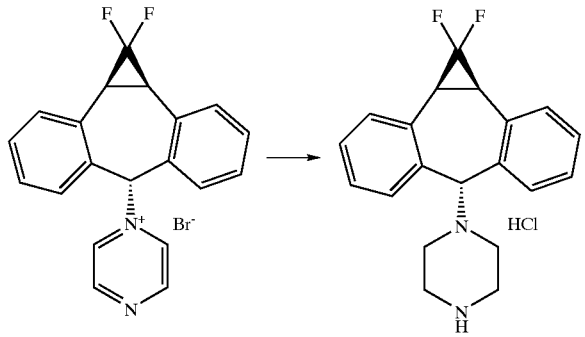

A stirred slurry of the pyrazinium salt from above (10.0 g, 24.9 mmol) in EtOAc (50 mL) was treated directly with NaBH$_4$ (2.07 g, 54.8 mmol, 2.2 equiv) and the slurry was cooled to 15° C. (cold-water bath). Trifluoroacetic acid (6.34 mL, 82.3 mmol, 3.30 equiv) was added drop-wise over a 15 minute period with the reaction temperature maintained between 22 and 25° C. during addition with periodic cooling (cold-water bath). Upon completion of addition, the reaction was allowed to stir at ambient temperature for 1.5 hours. At this time the reaction was cooled to 10° C. and quenched by cautious addition of 2.5 M NaOH (50 mL). The mixture was stirred at room temperature for 15 minutes and the layers were separated. The organic phase was washed with 2.5 M NaOH (2×50 mL), 50% saturated NaCl solution (50 mL) and dried (Na$_2$SO$_4$-6.0 g). EtOAc (50 mL) was added to the organic phase during the above workup from various transfers and washes, giving a total EtOAc volume of 80–100 mL at the end of the workup. This solution was treated with concentrated HCl (2.08 mL of a 12 M solution, 24.9 mmol, 1.0 equiv.) and the slurry was stirred at room temperature for 2 hours then at 0–5° C. for 15 min. White solid was filtered, washed with cold EtOAc (10 mL) and dried to provide the product as a powder, m.p. 274–278° C. (dec) (7.67 g with a potency of 85.6%, or 6.56 g corrected for free-base, 81%)

$^1$HNMR (500 MHz DMSO-$d_6$) δ9.41 (2H, br. s), 7.17–7.31 (8H, m), 4.17 (1H, s), 3.52 (2H, d, J=12.4 Hz), 3.11 (4H, br. s), 2.48–2.51 (4H, m)

$^{13}$CNMR (126 MHz DMSO-$d_6$) δ142.3, 133.4, 130.5, 129.6, 129.0, 128.4, 115.9, 113.6, 111.3, 76.2, 49.0, 43.6, 29.2, 29.1, 29.0; FD MS: m/e 326 (M+).

Anal. Calcd. For $C_{20}H_{21}ClF_2N_2$: C, 66.20; H, 5.83; N, 7.72.

Found: C, 66.08; H, 5.90; N, 7.72.

Combined Steps (f) and (g)

(2R)-anti-1-[4-(10,11-difluoromethano-10,11-dihydro-5H-dibenzo[a,d]cyclohepten-5-yl)-piperazin-1-yl]-3-quinolin-5-yloxy)-propan-2-ol trihydrochloride A suspension of 1,1-difluoro-6[1-piperazinyl]-1,1aa,6a,10ba-tetrahydrodibenzo[a,e]cyclopropa[c]-cycloheptene hydrochloride (5.41 g, 14.9 mmol) and powdered sodium carbonate (3.16 g, 29.8 mmol) in 54 mL of 3A ethanol was stirred at ambient temperature for 1 hour. (2R)-1-(5-Quinolinyloxy)-2,3-epoxypropane (3.00 g, 14.9 mmol) was added in one portion and the reaction mixture was heated to 65° C. for 19 hours. HPLC analysis (Gradient system with solvent A (acetonitrile) and solvent B (0.02M sodium monophosphate buffer containing 0.1% triethylamine adjusted to pH 3.5 with phosphoric acid) as follows: 0–12 min, 30% solvent A/70% solvent B; 12–30 min, linear gradient from 30% to 55% solvent A/70% to 45% solvent B; 30–35 min, 55% solvent A/45% solvent B, 1 mL/min, 1=240 nm, Synchropak SCD-100 25 cm×4.6 mm column) indicated total consumption of starting material. The mixture was allowed to cool to room temperature, filtered through a pre-wetted (EtOH) 14 gram plug of silica gel, and eluted with an additional 90 mL of ethanol. The filtrate was concentrated to a volume of approximately 60 mL and heated to 65° C. with stirring. A solution of HCl in ethanol (16.1 g at 0.135 g/g of solution, 59.6 mmol) was added drop-wise over 10 minutes and the resultant product solution was seeded, causing the trihydrochloride salt to precipitate. The mixture was allowed to cool to ambient temperature and stirred slowly for 2 hours. The precipitate was filtered, washed with ethanol, and dried in vacuo at 50° C. to give the crude trihydrochloride salt which was further purified by recrystallization from methanol/ethyl acetate to provide 7.45 g (78.4%) of (2R)-anti-1-[4-(10,11-difluoromethano-10,11-dihydro-5H-dibenzo[a,d]cyclohepten-5-yl)-piperazin-1-yl]-3-quinolin-5-yloxy)-propan-2-ol trihydrochloride as a solid.

Although the use of the syn 10,11-difluorodibenzomethanosuberol and the anti 5-bromo-10,11-difluoromethanodibenzosuberane have been described and exemplified above, the skilled artisan will appreciate that formation of the anti-pyrazinium salt compound of formula (6) can be effectively accomplished with either the syn or the trans isomer of 5-halo-10,11-(optionally substituted)methanodibenzosuberane compound of formula (5). This is possible by virtue of the intermediacy of a 10,11-(optionally substituted)methanodibenzosuberane tropylium ion in the formation of the anti-pyrazinium salt compound of formula (6).

Likewise, one skilled in the art is aware that the use of the syn isomer of 10,11-(optionally substituted)-methanodibenzosuberol (4) is not critical to the practice of this invention. The anti isomer of 10,11-(optionally substituted)methanodibenzosuberol would be equally effective. This is because the formation of 5-halo-10,11-(optionally substituted)-methanodibenzosuberane (5) proceeds via the corresponding tropylium ion intermediate which in the case of the bromide provides the anti isomer of the compound of formula (5) preferentially, by the method of this invention.

Additionally, the present invention provides a novel hydrate crystal form of (2R)-anti-5-{3-[4-(10,11-difluoromethanodibenzosuber-5-yl)piperazin-1-yl]-2-hydroxypropoxy}quinoline trihydrochloride ("Hydrate I"). A number of methods are available to characterize crystalline forms of organic compounds. Among these methods are differential scanning calorimetry, solid state NMR spectrometry, infra-red spectroscopy, and x-ray powder diffraction. The x-ray powder diffraction pattern is very useful for distinguishing between different crystalline forms of a compound.

X-ray powder diffraction analysis can be readily performed as follows. After lightly grinding the sample with an agate mortar and pestle, the sample is loaded into a sample holder for the x-ray powder diffraction measurement. The x-ray powder diffraction patterns are measured using a Siemens D5000 x-ray powder diffractometer equipped with a CuKα source ($\lambda$=1.54056 Å). A NIST traceable digital hygrometer (model 11-661-16) was used to measure the actual relative humidity in the sample chamber. The 0% R.H. XRD patterns were obtained by pre-drying the samples over $P_2O_5$ for at least one week. Interplanar spacings and peak intensities for the most prominent features were measured using a double-derivative peak picking method. Hydrate I has a typical XRD pattern with the following interplanar spacings (d) in Angstroms, wherein the interplanar spacings have the following typical relative intensities ($I/I_o$). The error of measurement is +/−0.04 Å. X-ray peaks with $I/I_o$ of 5% or greater were reported in Table 1, below. The cutoff was chosen arbitrarily.

TABLE 1

| d value Angstrom | $I/I_o$ (%) |
| --- | --- |
| 29.89 | 6.6 |
| 9.93 | 14.8 |
| 7.95 | 100 |
| 7.69 | 6.9 |
| 7.40 | 15.8 |
| 7.22 | 7.9 |
| 6.61 | 8.4 |
| 5.95 | 6.7 |
| 5.08 | 5.5 |
| 4.45 | 9.1 |
| 3.99 | 5.4 |
| 3.96 | 11.2 |
| 3.83 | 6.6 |
| 3.68 | 6.3 |
| 3.96 | 11 |
| 3.55 | 5.6 |
| 3.36 | 10.4 |

It is well known in the crystallography art that, for any given crystal form, the relative intensities of the diffraction peaks may vary due to a number of factors, including the effects of preferred orientation which result from a particular crystal morphology, and particle size. Where the effects of preferred orientation and/or particle size are present, peak intensities (that is, the $I/I_o$ value) are altered, but the characteristic peak positions of the polymorph are unchanged. See, e.g., The United States Pharmacopoeia #23, National Formulary #18, pages 1843–1844, 1995.

The effects of preferred orientation can be greatly reduced using a sample that is prepared in a manner that minimizes this effects, such as the use of a well ground sample. Hydrate I may be characterized as having an X-ray diffraction pattern which comprises peaks corresponding to the following d spacings: 7.95+/−0.04 Å when obtained at 22±2° C. and 31±10% relative humidity from a copper radiation source. Preferably, a properly prepared sample of Hydrate I may be characterized as having an X-ray diffraction pattern which comprises peaks corresponding to the following d spacings: 9.93, 7.95, 4.45, and 3.36+/−0.04 Å when obtained at 22±2° C. and 31±10% relative humidity from a copper radiation source.

Additionally, as the skilled artisan would appreciate, Hydrate I may also be characterized by solid state NMR spectroscopy. Solid state NMR ($^{13}C$) analysis was performed using a Varian Unity 400 MHz spectrometer operating at a carbon frequency of 100.580 MHz, equipped with a complete solids accessory and Varian 7 mm VT CP/MAS probe. Acquisition parameters were as follows: 90° proton r.f. pulse width 4.0 $\mu$s, contact time 1.0 ms, pulse repetition time 5 s, MAS frequency 7.0 kHz, spectral width 50 kHz, and acquisition time 50 ms. Chemical shifts were referenced to the methyl group of hexamethylbenzene ($\delta$=17.3 ppm) by sample replacement. Solid state $^{13}C$ chemical shifts reflect not only the molecular structure of Hydrate I, but also the electronic environment of the molecule in the crystal. The diagnostic $^{13}C$ resonances of Hydrate I, which appear in the 100–160 ppm chemical shift range, are 105.7, 106.5, 111.0, 113.0, 118.8, 119.5, 130.0, 132.3, 133.7, 134.7, 136.4, 136.7, 141.3, 142.6, 145.8, 148.1, 152.6, and 153.6 ppm.

The precise conditions under which Hydrate I is formed may be empirically determined and it is only possible to give a number of methods which have been found to be suitable in practice. Thus, for example, Hydrate I may be prepared by crystallization under controlled conditions. It is understood that the present process can utilize (2R)-anti-5-{3-[4-(10,11-difluoromethanodibenzosuber-5-yl)piperazin-1-yl]-2-hydroxypropoxy}quinoline trihydrochloride regardless of its hydration state or crystalline state. In particular, it can be prepared either from (2R)-anti-5-{3-[4-(10,11-difluoromethanodibenzosuber-5-yl)piperazin-1-yl]-2-hydroxypropoxy}quinoline trihydrochloride or by recrystallization of previously isolated (2R)-anti-5-{3-[4-(10,11-difluoromethanodibenzosuber-5-yl)piperazin-1-yl]-2-hydroxypropoxy}quinoline trihydrochloride. Mixtures of water and water-miscible solvents are used for the crystallization of Hydrate I. In general, the use of water miscible solvents such as alkyl ketones, e.g. acetone, butanone, and the like; alkyl nitrites, e.g. acetonitrile, propionitrile, and the like; and alkyl alcohols, e.g. methanol, ethanol, isopropanol, and the like; is preferred. In order to dissolve the starting material it may be helpful to warm the solvent system.

It may be advantageous to add "seeds" of Hydrate I to the solution in order to induce crystallization. Hydrate I is readily soluble and can be filtered off from the crystallization solution, if desired after cooling, and washed and dried. If desired, Hydrate I prepared as above may be further crystallized using similar conditions for crystallization to those described above.

The present invention is further illustrated by the following examples and preparations. These examples and preparations are illustrative only and are not intended to limit the invention in any way.

Hydrate I was prepared by recrystallizing a compound of Example 1, as obtained by the previously defined process, as an ethanol wetcake, vacuum dried, then humidified to replace the ethanol. Therefore the present invention further encompasses a process of preparing Hydrate I comprising: a) forming an ethanol wetcake of (2R)-anti-5-{3-[4-(10,11-difluoromethanodibenzosuber-5-yl)piperazin-1-yl]-2-hydroxypropoxy}quinoline trihydrochloride, b) drying the ethanol wetcake by vacuum to obtain dry (2R)-anti-5-{3-[4-(10,11-difluoromethanodibenzosuber-5-yl)piperazin-1-yl]-2-hydroxypropoxy}quinoline trihydrochloride, and c) humidifying the dry (2R)-anti-5-{3-[4-(10,11-difluoromethanodibenzosuber-5-yl)piperazin-1-yl]-2-hydroxypropoxy}quinoline trihydrochloride to obtain Hydrate I.

The following solvates may be converted to Hydrate I by humidification to replace the organic solvents. This list of solvates are for example purposes only. The skilled artisan will appreciate that the organic solvents used for recrystallization are non-specific and maybe used in a multitude of combinations.

Methanol/$H_2O$ solvate was prepared by dissolving a compound of Example 1 in MeOH (10 mL) at ambient temperature with stirring. To the stirred solution was added EtOAc (20 mL). The product wetcake was isolated by vacuum filtration, washed with EtOAc (15 mL) and dried in a vacuum oven at ambient temperature for ~16 hours. Yield= 579 mg.

Ethanol/$H_2O$ solvate was prepared by suspending a compound of Example 1 in 3A EtOH (20 mL). The stirred suspension was heated to reflux and additional 3A EtOH (10 mL) was added to dissolve the solids. The solution was allowed to reflux (78.5° C.) for ~20 minutes, at which time the heat source was turned off and the solution was allowed to slowly cool to room temperature. The solution became turbid by ~36° C. The microcrystalline product was isolated by vacuum filtration, washed with 3A EtOH (2–3 mL), and air dried. Yield=141 mg (significant product loss accompanied transfer of the highly electrostatic particles).

IPA/$H_2O$ solvate was prepared by dissolving a compound of Example 1 in MeOH (10 mL) at ambient temperature with stirring. To the stirred solution was added IPA (10 mL) dropwise to induce crystallization. The solid product was isolated by vacuum filtration, washed with IPA (20 mL), and dried in a Buchner funnel over an air stream. Yield=509 mg.

n-Propanol/$H_2O$ solvate was prepared by dissolving a compound of Example 1 in $H_2O$ (1 mL) and n-PrOH (1 mL). To the stirred solution was added n-PrOH (68 mL). The solution was then rotovapped to dryness to produce a tacky solid. n-PrOH (20 mL) was added and the solid product was isolated by vacuum filtration, washed with n-PrOH (5 mL), and air-dried. Yield=293 mg.

THF/$H_2O$ solvate was prepared by dissolving a compound of Example 1 in MeOH (10 mL) at ambient temperature with stirring. To the stirred solution was added THF (20 mL) dropwise to induce crystallization. The solid product was isolated by vacuum filtration, washed with THF (20 mL), and dried in a Buchner funnel over an air stream. Yield=520 mg.

Acetone/$H_2O$ solvate was prepared by dissolving a compound of Example 1 in MeOH (10 mL) at ambient temperature with stirring. To the stirred solution was added acetone (20 mL) dropwise to induce crystallization. The solid product was isolated by vacuum filtration, washed with acetone (15 mL), and dried in a Buchner funnel over an air stream. Yield=472 mg.

Acetonitrile/$H_2O$ solvate was prepared by suspending a compound of Example 1 in ACN (25 mL). The stirred suspension was then heated and $H_2O$ (3 mL) was added to dissolve the solids. The solution was cooled to ambient temperature, at which time EtOAc (50 mL) was added dropwise. The solid product was isolated by vacuum filtration, washed with EtOAc (5 mL), and air-dried. Yield= 555 mg.

DMAC/acetone/$H_2O$ solvate was prepared by dissolving a compound of Example 1 in DMAC (5 mL) with stirring at ambient temperature. A small amount of undissolved, gummy solid was removed by gravity filtration. Acetone (20 mL) was then added dropwise to the stirred solution and the resulting solid was allowed to slurry overnight. The yellow solid was isolated by vacuum filtration onto cellulose acetate filter paper and washed with acetone. Yield=389 mg.

DMF/$H_2O$ solvate was prepared by suspending a compound of Example 1 in DMF (13 mL) and water (~0.2 mL) was added dropwise to the stirred suspension, effecting rapid dissolution of the solids. Crystallization was induced by dropwise addition of $^i$PrOAc (15 mL) followed by continued slurrying for 24 hrs. The solid product was isolated by vacuum filtration and washed with $^i$PrOAc. The tacky yellow solid was characterized as a wetcake.

DMSO/ACN/$H_2O$ solvate: a compound of Example 1 was dissolved in DMSO (3 mL) with stirring at room temperature. ACN (20 mL) was then added dropwise to the stirred solution. The solid product was isolated by filtration onto cellulose acetate filter paper and washed with several mL of ACN. The resulting wetcake was dried at 50° C. for 20 min. to give 284 mg of bright yellow powder.

The present invention further provides a method of treatment for a drug resistant disease comprising coadministering to a mammal in need thereof a resistance modulating amount of Hydrate I and an effective amount of a treatment drug for said drug resistant disease. Preferably the disease is cancer. Preferably, the treatment drug is a cancer chemotherapeutic agent.

The present invention further provides a method of treatment for a multidrug resistant disease comprising coadministering to a mammal in need thereof a multidrug resistance modulating amount of Hydrate I and an effective amount of a treatment drug for said multidrug resistant disease. Preferably, the treatment drug is a cancer chemotherapeutic agent.

The present invention further provides a method for enhancing bioavailability of a pharmaceutically active agent to the brain, comprising coadministering to a mammal in need thereof a therapeutically effective amount of said drug and Hydrate I sufficient enough to allow said drug to cross the blood-brain barrier and enter the brain. Preferable the active agent is an HIV protease inhibitor. Examples of such protease inhibitors contemplated by the present invention are NELFINAVIR, which is preferably administered as the mesylate salt at 750 mg three times per day (U.S. Pat. No. 5,484,926, herein incorporated by reference); RITONAVIR, which is preferably administered at 600 mg twice daily (U.S. Pat. No. 5,484,801, herein incorporated by reference); SAQUINAVIR, which is preferably administered at the mesylate salt at 1,200 mg three times per day (U.S. Pat. No. 5,196,438, herein incorporated by reference); INDINAVIR, which is preferably administered as the sulfate salt at 800 mg three times per day (U.S. Pat. No. 5,413,999, herein incorporated by reference); and AMPRENAVIR, which is preferably administered at 1,200 mg twice daily (U.S. Pat. No. 5,585,397, herein incorporated by reference). The skilled artisan would recognize that this list is not exhaustive. Additionally, the skilled artisan would recognize that the protease inhibitors' administration to a patient may vary from the preferred.

The present invention further provides the use of Hydrate I in combination with an effective amount of a treatment drug, or a pharmaceutically acceptable salt thereof, for the manufacture of a medicament for the treatment of a drug resistant disease. Preferably the disease is cancer. Preferably, the treatment drug is a cancer chemotherapeutic agent.

The invention further provides the use of Hydrate I in combination with an effective amount of a treatment drug, or a pharmaceutically acceptable salt thereof, for the manufacture of a medicament for the treatment of a multidrug resistant disease. Preferably, the treatment drug is a cancer chemotherapeutic agent.

The present invention further provides the use of Hydrate I in combination with a pharmaceutically active agent, or a pharmaceutically acceptable salt thereof, for the manufacture of a medicament for enhancing bioavailability of the pharmaceutically active agent to the brain, comprising coadministering to a mammal in need thereof a therapeutically effective amount of said drug and Hydrate I sufficient enough to allow said drug to cross the blood-brain barrier and enter the brain. Preferable the active agent is an HIV protease inhibitor.

Preferably, the present invention relates to a pharmaceutical formulation comprising Hydrate I; one or more pharmaceutical carriers, diluents, or excipients; and optionally a treatment drug.

When employed as a pharmaceutical, Hydrate I is usually administered in the form of pharmaceutical compositions. These compositions can be administered by a variety of routes including oral, rectal, transdermal, and intranasal. Such compositions are prepared in a manner well known in the pharmaceutical art and comprise Hydrate I.

The term "substantially pure" refers to the crystal phase purity of Hydrate I. In practice we have found that small amounts of other crystalline forms do not adversely affect the advantageous properties of Hydrate I. According to the present invention substantially pure refers to Hydrate I which is greater than 90%, preferably greater than 95% of the total crystalline material.

This invention also includes pharmaceutical compositions which contain Hydrate I (referred to as "active ingredient" herein below) associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid or semi-solid which acts as a vehicle, carrier, or medium for the active ingredient. Thus, the compositions can be in the form of tablets, pills, powders, lozenges, sachets, cachets, emulsions, aerosols, ointments containing, for example, up to 10% by weight of the active compound, tablet, soft and hard gelatin capsules, suppositories, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 mg to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, Hydrate I is employed at no more than about 20 weight percent of the pharmaceutical composition, more preferably no more than about 15 weight percent, with the balance being pharmaceutically inert carrier(s).

Hydrate I is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing compositions such as tablets, the active ingredient is mixed with a pharmaceutical excipient to form a solid pre-formulation composition containing a homogeneous mixture of a compound of the present invention. When referring to these pre-formulation compositions as homogeneous, it is meant that the active ingredient is dispersed evenly throughout the composition so that the composition may be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include liquids, suspensions, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention which comprise Hydrate I, as active ingredient.

Formulation Example 1

Hard gelatin capsules containing the following ingredients are prepared:

| Ingredient | (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |

-continued

| Ingredient | (mg/tablet) |
| --- | --- |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation Example 5

Capsules, each containing 40 mg of medicament are made as follows:

| Ingredient | (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

| Ingredient | (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 560 mg quantities.

Formulation Example 9

A subcutaneous formulation may be prepared as follows:

| Ingredient | Quantity |
|---|---|
| Active Ingredient | 1.0 mg |
| corn oil | 1 ml |

Formulation Example 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in Remington's Pharmaceutical Sciences, Mace Publishing Company, Philadelphia, Pa., 17th ed. (1985).

As noted above, Hydrate I is suitable for use in a variety of drug delivery systems described above. Additionally, in order to enhance the in vivo serum half-life of the present compound, it may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The amount of Hydrate I administered to the patient will vary depending upon the purpose of the administration, such as prophylaxis or therapy, the state of the patient, the manner of administration, and the like. In therapeutic applications, compositions are administered to a patient already suffering from Alzheimer's disease in an amount sufficient to at least partially arrest further onset of the symptoms of the disease and its complications. An amount adequate to accomplish this is defined as "therapeutically effective dose." Amounts effective for this use will depend on the judgment of the attending clinician depending upon factors such as the degree or severity of the disease state in the patient, the age, weight and general condition of the patient, and the like. Preferably, for use as therapeutics, Hydrate I is administered at dosages ranging from about 1 to about 500 mg/kg/day.

The present invention provides a process for preparing Hydrate I which comprises crystallizing (2R)-anti-5-{3-[4-(10,11-difluoromethanodibenzosuber-5-yl)piperazin-1-yl]-2-hydroxypropoxy}quinoline trihydrochloride from a solution of water and a water miscible solvent under conditions which yields Hydrate I.

We claim:

1. A process for preparing a compound of formula (1)

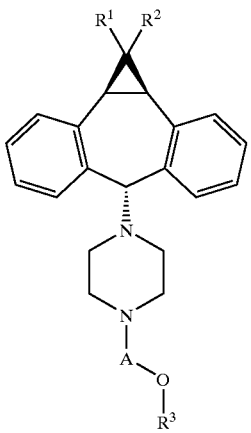

wherein

A is —$CH_2$—$CH_2$—, —$CH_2$—$CHR^a$—$CH_2$—, —$CH_2$—$CHR^a$—$CH_2$—$CH_2$—, and $R^a$ is OH;

$R^1$ is H, F, Cl, or Br;

$R^2$ is H, F, Cl, or Br; and $R^3$ is heteroaryl or phenyl, each optionally substituted with F, Cl, Br, $CF_3$, CN, $NO_2$, or $OCHF_2$;

or the pharmaceutically acceptable salts thereof, comprising the steps of:

(a) reacting a compound of formula (4)

(4)

with a nucleophile source to form a compound of formula (5)

(5)

wherein X is a leaving group;

(b) reacting a compound of formula (5) with pyrazine to provide a compound of formula (6)

(6)

(c) reducing the compound of formula (6) to provide a compound of formula (8):

(8)

(d) reacting a compound of formula (8) with either:

(i) an epoxy compound of formula (9)

$$\text{epoxide}-(CH_2)_n-O-R^3$$ (9)

wherein $R^3$ is as defined above, and n is an integer 1 or 2; or (ii) a halo compound of formula (10)

$$X^1-(CH_2)_m-O-R^3$$ (10)

wherein $R^3$ is as defined above, $X^1$ is halo, and m is 2, 3 or 4; and (e) optionally forming a pharmaceutically acceptable salt from the compound produced in step (d).

2. The process of claim 1 wherein, the leaving group of step (a) is selected from the group consisting of Br, Cl, OMs and OTs.

3. The process of claim 1 wherein $R^1$ and $R^2$ are each F and X is Br.

4. The process of claim 1 wherein $R^3$ is quinolin-5-yl.

5. The process of claim 4, wherein the salt of a compound of formula (1) is the trihydrochloride salt.

6. The process of claim 2 wherein $R^3$ is quinolin-5-yl.

7. The process of claim 6, wherein the salt of a compound of formula (1) is the trihydrochloride salt.

8. The process of claim 3 wherein $R^3$ is quinolin-5-yl.

9. The process of claim 8, wherein the salt of a compound of formula (1) is the trihydrochloride salt.

10. A process for preparing a compound of formula (6)

wherein $R^1$ and $R^2$ are independently H, F, Cl or Br and X is a leaving group comprising the steps of:

(a) reacting a compound of formula (4)

(4)

with a nucleophile source to form a compound of formula (5);

(b) reacting a compound of formula (5)

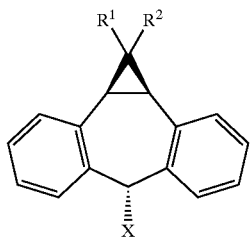

wherein X is a leaving group, with pyrazine to form the compound of formula (6)

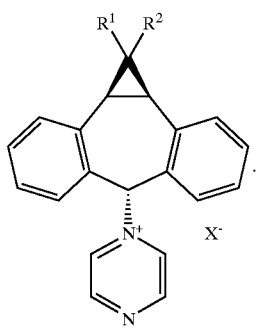

11. A process according to claim 10 further comprising: reducing a compound of formula (6) to provide a compound of formula (8)

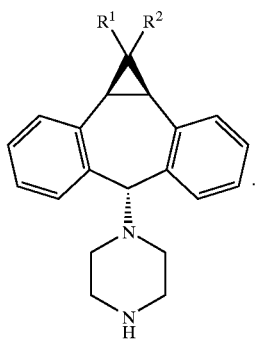

12. A compound of formula (6):

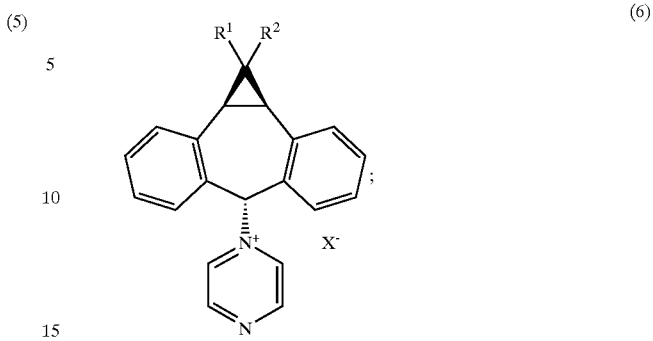

wherein $R^1$ and $R^2$ are independently H, F, Cl or I, Br and X is selected from the group consisting of I, Br, Cl, OMs, and OTs.

13. A compound of claim 12 wherein $R^1$ and $R^2$ are both F and X is Br.

14. A process for preparing a compound of formula (8):

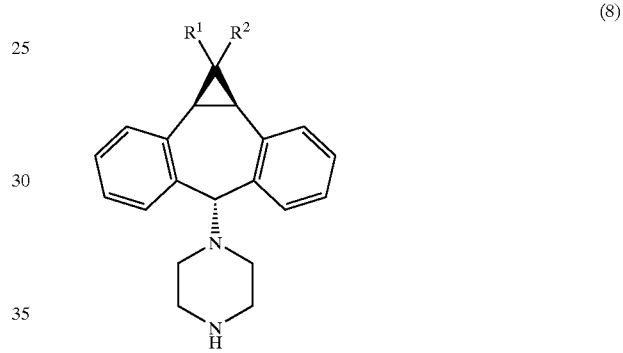

wherein $R^1$ and $R^2$ are independently H, F, Cl or Br

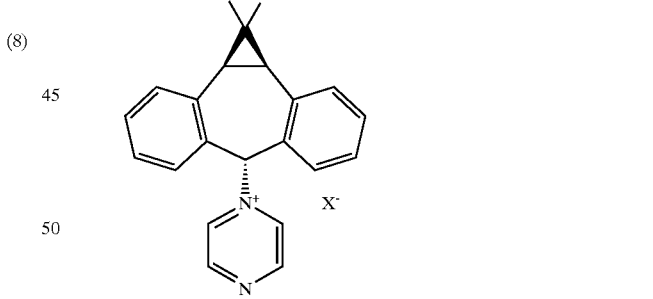

wherein X is a leaving group.

15. A compound of claim 14 wherein $R^1$ and $R^2$ are both F.

* * * * *

UNITED STATES PATENT AND TRADEMARK OFFICE
CERTIFICATE OF CORRECTION

PATENT NO.   : 6,521,755 B1  Page 1 of 1
DATED        : February 18, 2003
INVENTOR(S)  : Bret Eugene Huff et al.

It is certified that error appears in the above-identified patent and that said Letters Patent is hereby corrected as shown below:

<u>Column 38,</u>
Line 38, after the words "…are independently H, F, Cl or Br" please insert the following -- by reducing the compound of formula (6). --.

Signed and Sealed this

Seventh Day of October, 2003

JAMES E. ROGAN
*Director of the United States Patent and Trademark Office*